US012215335B2

(12) United States Patent
Williams et al.

(10) Patent No.: US 12,215,335 B2
(45) **Date of Patent: *Feb. 4, 2025**

(54) NON-INTEGRATING DNA VECTORS FOR THE GENETIC MODIFICATION OF CELLS

(71) Applicant: Deutsches Krebsforschungszentrum, Heidelberg (DE)

(72) Inventors: James A. Williams, Lincoln, NE (US); Matthias Bozza, Heidelberg (DE); Richard Harbottle, Ladenburg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 950 days.

This patent is subject to a terminal disclaimer.

(21) Appl. No.: 16/648,885

(22) PCT Filed: Sep. 17, 2018

(86) PCT No.: PCT/US2018/051381

§ 371 (c)(1),
(2) Date: Mar. 19, 2020

(87) PCT Pub. No.: WO2019/060253

PCT Pub. Date: Mar. 28, 2019

(65) Prior Publication Data

US 2020/0277624 A1 Sep. 3, 2020

(30) Foreign Application Priority Data

Sep. 19, 2017 (EP) .................................... 17191829

(51) Int. Cl.
*C12N 15/85* (2006.01)
*C12N 15/67* (2006.01)
*C12N 15/79* (2006.01)

(52) U.S. Cl.
CPC ............ *C12N 15/85* (2013.01); *C12N 15/79* (2013.01); *C12N 15/67* (2013.01); *C12N 2800/106* (2013.01); *C12N 2800/108* (2013.01); *C12N 2820/55* (2013.01); *C12N 2830/46* (2013.01)

(58) Field of Classification Search
CPC .... C12N 2830/46; C12N 15/85; C12N 15/00; C12N 15/67; C12N 15/79; C12N 2800/108; C12N 2800/106; C12N 15/86; C12N 2820/55; C12N 2830/42; C12N 15/907; C12N 15/625; C12N 2740/15043; C12N 15/113; C12N 2800/22; C12N 2830/20; C12N 2740/10043; C12N 2820/80; C12N 2820/85; A61K 48/0066; A61K 48/00; C07K 2317/569; C07K 2317/72; C07K 2317/732; C07K 2318/20; C07K 14/705; A61P 31/00; A61P 35/00; A61P 37/00

See application file for complete search history.

(56) References Cited

U.S. PATENT DOCUMENTS

| | | | | |
|---|---|---|---|---|
| 5,922,583 | A | 7/1999 | Morsey | |
| 5,985,607 | A | 11/1999 | Delcuve et al. | |
| 6,410,314 | B1 | 6/2002 | Baiker et al. | |
| 6,977,174 | B2 | 12/2005 | Crouzet et al. | |
| 7,244,609 | B2 | 7/2007 | Drocourt et al. | |
| 7,611,883 | B2 | 11/2009 | Cranenburgh | |
| 2006/0063232 | A1 | 3/2006 | Grabherr et al. | |
| 2009/0158450 | A1 | 6/2009 | Lavitrano et al. | |
| 2010/0018415 | A1 | 1/2010 | Wincott et al. | |
| 2011/0097798 | A1 | 4/2011 | Li et al. | |
| 2013/0244280 | A1 | 9/2013 | Parikh et al. | |
| 2015/0191735 | A1* | 7/2015 | Williams | C12N 15/635 435/69.3 |
| 2015/0275221 | A1 | 10/2015 | Williams | |
| 2015/0322439 | A1* | 11/2015 | Williams | C12N 15/63 435/320.1 |
| 2016/0215296 | A1* | 7/2016 | Williams | C12P 19/34 |
| 2022/0226506 | A1* | 7/2022 | Bozza | A61K 48/0066 |

FOREIGN PATENT DOCUMENTS

| | | | |
|---|---|---|---|
| EP | 2476755 | A1 | 7/2012 |
| JP | 2009511010 | A | 3/2009 |
| JP | 2016208845 | A | 12/2016 |
| KR | 20130094830 | A | 8/2013 |
| WO | 2005100604 | A2 | 10/2005 |
| WO | 2006048291 | A2 | 5/2006 |
| WO | 2008153733 | A2 | 12/2008 |
| WO | 2010018444 | A2 | 2/2010 |

(Continued)

OTHER PUBLICATIONS

Argyros, O. et al. "Non-viral episomal modification of cells using S/MAR elements". Expert Opinion on Biological Therapy. vol. 11 , No. 9 (May 2011), pp. 1177-1191 (Year: 2011).*

(Continued)

*Primary Examiner* — Joseph G. Dauner
*Assistant Examiner* — Alexandra Geraldine Dace Denito
(74) *Attorney, Agent, or Firm* — Taft Stettinius & Hollister LLP

(57) ABSTRACT

The present invention relates to a polynucleotide comprising at least one promoter and an S/MAR element, wherein the S/MAR element is located downstream of the promoter in the 3' UTR of the transcription unit and wherein the S/MAR element is flanked by a 5' splice donor site and a 3' splice acceptor site; the present invention further relates to a composition comprising the polynucleotide, and to the polynucleotide for use in medicine and for use in treating genetic disease.

27 Claims, 12 Drawing Sheets

Specification includes a Sequence Listing.

(56) References Cited

FOREIGN PATENT DOCUMENTS

| | | | |
|---|---|---|---|
| WO | 2014016580 | A1 | 1/2014 |
| WO | 2014035457 | A1 | 3/2014 |
| WO | 2014077863 | A1 | 5/2014 |
| WO | 2014077866 | A1 | 5/2014 |
| WO | 2015078999 | A1 | 6/2015 |

OTHER PUBLICATIONS

Shaul, O. "How Introns enhance gene expression". International Journal of Biochemistry and Cell Biology, vol. 91 (2017), pp. 145-155 (Year: 2017).*
Prel, A. et al. "Influence of untranslated regions on retroviral mRNA transfer and expression." BMC Biotechnology, vol. 13 (2013), p. 35 (Year: 2013).*
Pagés, J.C. et al. "Toolbox for retrovectorologists". The Journal of Gene Medicine, vol. 6 (2004), pp. S67-S82 (Year: 2004).*
Extended European Search Report; European Patent Office; European Application No. 22201555.4; May 2, 2023; 10 pages.
International Search Report; European Patent Office; International Application No. PCT/US2018/051381; Nov. 29, 2018; 5 pages.
Written Opinion of the International Searching Authority; European Patent Office; International Application No. PCT/US2018/051381; Nov. 29, 2018; 7 pages.
Decision of Patent; Japanese Patent Office; Japanese Application No. 2020-516608; Mar. 14, 2023; 5 pages.
Matthias Bozza; Dissertation entitled The Development of a Novel S/MAR DNA Vector Platform for the Stable, Persistent and Safe Genetic Engineering of Dividing Cells; Submitted to the Combined Faculties for the Natural Science and for Mathematics of the Ruperto-Carola University of Heidelberg, Germany; Aug. 1, 2018; 163 pages.
Alicia Roig-Merino; Dissertation entitled Genetic Modification of Stem Cells Utilizing S/MAR DNA Vectors; Submitted to the Combined Faculties for the Natural Sciences and for Mathematics of the Ruperto-Carola University of Heidelberg, Germany; Sep. 6, 2018; 303 pages.
Salina Arope et al.; Molecular Characterization of a Human Matrix Attachment Region Epigenetic Regulator; Plos One; Nov. 2013; 11 pages; vol. 8, Issue 11.
Lucy W. Barrett et al.; Regulation of Eukaryotic Gene Expression by the Untranslated Gene Regions and Other Non-Coding Elements; Cellular and Molecular Life Sciences; 2012; 22 pages; vol. 69.
Ramu Chenna et al.; Multiple Sequence Alignment with the Clustal Series of Programs; Nucleic Acids Research; 2003; 4 pages; vol. 31, No. 13.
Kamil J. Cygan et al.; Messenger RNA Splicing Signals; eLS; John Wiley & Sons; Feb. 2017; 8 pages.
Anja Ehrhardt et al.; Episomal Vectors for Gene Therapy; Current Gene Therapy; 2008; 15 pages; vol. 8.
Thomas Franch et al.; U-Turns and Regulatory RNAs; Current Opinion in Microbiology; 2000; 6 pages; vol. 3.
Rudolf Haase et al.; pEPito: A Significantly Improved Non-Viral Episomal Expression Vector for Mammalian Cells; BMC Biotechnology; 2010; 14 pages; vol. 10, No. 20.
Ted H. J. Kwaks et al.; Identification of Anti-Repressor Elements That Confer High and Stable Protein Production in Mammalian Cells; Nature Biotechnology; May 2003; 8 pages; vol. 21.
Herve Le Hir et al.; How Introns Influence and Enhance Eukaryotic Gene Expression; Elsevier; Trends in Biochemical Sciences; Apr. 2003; 6 pages; vol. 28, No. 4.
I. Liebich et al.; Evaluation of Sequence Motifs Found in Scaffold/Matrix-Attached Regions (S/MARs); Nucleic Acids Research; 2002; 10 pages; vol. 30, No. 15.
Ziqing Liu et al.; Systematic Comparison of 2A Peptides for Cloning Multi-Genes in a Polycistronic Vector; Scientific Reports; May 19, 2017; 9 pages.
Jiamiao Lu et al.; A Mini-Intronic Plasmid (Mip): A Novel Robust Transgene Expression Vector In Vivo and In Vitro; Molecular Therapy; May 2013; 10 pages; vol. 21, No. 5.
Jeremy M. Luke et al.; Vector Insight-Targeted Integrative Antisense Expression System for Plasmid Stabilization; Mol Biotechnol; 2011; 7 pages; vol. 47.
Uta Müller-Kuller et al.; A Minimal Ubiquitous Chromatin Opening Element (UCOE) Effectively Prevents Silencing of Juxtaposed Heterologous Promoters by Epigenetic Remodeling in Multipotent and Pluripotent Stem Cells; Nucleic Acids Research; 2015; 16 pages; vol. 43, No. 3.
Vivek K. Mutalik et al.; Rationally Designed Families of Orthogonal RNA Regulators of Translation; Nature Chemical Biology; May 2012; 8 pages; vol. 8.
Dokyun NA et al.; Metabolic Engineering of *Escherichia coli* Using Synthetic Small Regulatory RNAs; Nature Biotechnology; Feb. 2013; 8 pages; vol. 31, No. 2.
C. Piechaczek et al.; A Vector Based on the SV40 Origin of Replication and Chromosomal S/MARs Replicates Episomally in CHO Cells; Nucleic Acids Research; 1999; 3 pages; vol. 27, No. 2.
Fay Saunders et al.; Chromatin Function Modifying Elements in an Industrial Antibody Production Platform—Comparison of UCOE, MAR, STAR and cHS4 Elements; Plos One; Apr. 7, 2015; 20 pages.
Santhosh Chakkaramakkil Verghese et al.; S/MAR Sequence Confers Long-Term Mitotic Stability on Non-Integrating Lentiviral Vector Episomes Without Selection; Nucleic Acids Research; 2014; 13 pages.
E. Gerhart H. Wagner et al.; Antisense RNAs in Bacteria and Their Genetic Elements; Advances in Genetics; 2002; 38 pages; vol. 46.
Adam G. West et al.; Insulators: Many Functions, Many Mechanisms; Genes & Development; 2002; 18 pages; vol. 16.
I. W. Wilson et al.; Importance of Structural Differences Between Complementary RNA Molecules to Control of Replication of an IncB Plasmid; Journal of Bacteriology; Feb. 1997; 12 pages; vol. 179, No. 3.
Suet-Ping Wong et al.; Genetic Modification of Dividing Cells Using Episomally Maintained S/MAR DNA Vectors; Molecular Therapy—Nucleic Acids; 2013; 12 pages; vol. 2.
Gloria Del Solar et al.; Replication and Control of Circular Bacterial Plasmids; Microbiology and Molecular Biology Reviews; Jun. 1998; p. 434-464; vol. 62, No. 2.
Isa M. Stehle et al.; Exploiting a Minimal System to Study the Epigenetic Control of DNA Replication: The Interplay Between Transcription and Replication; Chromosome Research; 2003; p. 413-421; vol. 11.
International Preliminary Report on Patentability; The International Bureau of WIPO; International Application No. PCT/US2018/051381; Mar. 24, 2020; 8 pages.
Notice of opposition; European Patent Office; European Application No. 17191829.5; May 20, 2021; 36 pages.
Ley, Déborah et al.; MAR Elements and Transposons for Improved Transgene Integration and Expression; PLoS One, Apr. 2013; 11 pages; vol. 8, No. 4.
Li, Qin et al.; A short synthetic chimeric sequence harboring matrix attachment region/PSAR2 increases transgene expression in Chinese hamster ovary cells; Bioscience, Biotechnology, and Biochemistry; 2017; 8 pages.
Noguchi, Chiemi et al.; Fusion of the Dhfr/Mtx and IR/MAR Gene Amplification Methods Produces a Rapid and Efficient Method for Stable Recombinant Protein Production; PLoS One; Dec. 2012; 14 pages; vol. 7, No. 12.
Qin, Jane Yuxia et al.; Systematic Comparison of Constitutive Promoters and the Doxycycline-Inducible Promoter; PLoS One; May 2010; 4 pages; vol. 5, No. 5.
Boulikas, Teni; Homeotic Protein Binding Sites, Origins of Replication, and Nuclear Matrix Anchorage Sites Share the ATTA and ATTTA Motifs; Journal of Cellular Biochemistry; 1992; pp. 111-123; vol. 50.
Boulikas, Teni; Nature of DNA Sequences at the Attachment Regions of Genes to the Nuclear Matrix; Journal of Cellular Biochemistry: 1993; pp. 14-22; vol. 52.

(56) References Cited

OTHER PUBLICATIONS

Voigtlander, Richard et al.; A Novel Adenoviral Hybrid-vector System Carrying a Plasmid Replicon for Safe and Efficient Cell and Gene Therapeutic Applications; Molecular Therapy-Nucleic Acids; 2013; 14 pages; vol. 2.
NCBI; *Homo sapiens* matrix attachment region 1-68 genomic sequence; 2008; 2 pages.
NCBI; Synthetic construct PSAR2 sequence; 2013; 1 page.
Argyros, Orestis et al.; Development of S/MAR minicircles for enhanced and persistent transgene expression in the mouse liver; J Mol Med; 2011; pp. 515-529; vol. 89.
Korean Decision for Grant, Korean Intellectual Property Office, Korean Patent Application No. 10-2020-7010722, Jul. 2, 2024, 6 pages.
Tian et al., Identification of a potent MAR element from the human genome and assessment of its activity in stably transfected CHO cells, J. Cell. Mol. Med. vol. 22, No. 2, 2018, pp. 1095-1102.

* cited by examiner

XhoI-S/MAR human IFN B-EcoRI
1973 bp

SD-hIFN B SMAR SA
2085 bp

SD SMAR (-AATAAA) SA
2085 bp

NON-INTEGRATING DNA VECTORS FOR THE GENETIC MODIFICATION OF CELLS

CROSS REFERENCE TO RELATED APPLICATIONS

This application is a U.S. National Phase of International PCT Application No. PCT/US2018/051381 filed Sep. 17, 2018, which claims priority to European Patent Application Serial No. 17191829.5, filed Sep. 19, 2017, the contents of each application are incorporated herein by reference in their entirety.

FIELD OF THE INVENTION

The present invention relates to a family of self-replicating non-integrative episomal vertebrate expression vectors useful for in gene therapy, ex vivo cell therapy, stem cell therapy, and more particularly, for improving the expression of vector encoded antigens or therapeutic genes.

Such recombinant DNA molecules are useful in biotechnology, transgenic organisms, gone therapy, stem cell therapy, therapeutic vaccination, agriculture and DNA vaccines.

BACKGROUND OF THE INVENTION

Genetic modification of cells is used routinely in modern cell culture for scientific purposes. However, use of corresponding techniques in treatment of inherited diseases caused by mutations of genes, while being highly desirable, still is hampered by the problem that methods available usually only provide transient modification, such as transient transfection protocols, whereas methods providing stable modification of cells such as with viral retroviral and lentiviral vectors or non-viral transposon vectors usually rely on integration of the transgene into the genome of the host cell. Integration of a transgene, however, even if targeted to a specific locus, bears the risk of inducing a deleterious mutation, which may lead e.g. to cancer as a side effect of treatment.

Scaffold/matrix attachment regions (S/MARs), which are also known as scaffold-attachment regions (SARs) or matrix-associated regions (MARs) are known as sequences in the genome of eukaryotic organisms mediating attachment of the nuclear matrix. The S/MARS are AT rich sequences, and some AT-rich motifs were found to be further enriched (Liebeich et al., (2002), NAR 30(15): 3433). A variety of vectors has been proposed for stable maintenance in cells based on S/MAR 30 motifs, e.g. in U.S. Pat. No. 6,410,314 B1 and in Haase et al., (2010), BMC Biotechnology 10:20; moreover, epigenetic effects having an influence on replication of such vectors were identified (Has se et al., (013) PLOS One 8(11):e79262). Nonetheless, S/MAR based vectors being stable enough for use in gene therapy are needed.

Suboptimal expression level, gene silencing and low establishment rate represent the major limitations of S/MAR based vectors described in the art.

There is, therefore a need for improved means and methods for stable transfection of cells, in particular using S/MAR elements and avoiding the risks involved with integration of the transgene into the genome of the host cell. This problem is solved by the means and methods disclosed herein.

SUMMARY OF THE INVENTION

The present invention relates to vectors useful for non-integrative episomal gene therapy and stem cell therapy, and more particularly, for improving transgene expression and vector establishment efficiency of a self-replicating non-integrative episomal S/MAR expression vector, and for eliminating antibiotic resistance marker gene transfer by non-viral vectors.

Improved vector methods and compositions that improve the expression and establishment efficiency of a self-replicating non-integrative episomal S/MAR expression vector in a target vertebrate cell are disclosed.

One object of the invention is to provide improved expression of a self-replicating non-integrative episomal S/MAR expression vector in a target vertebrate cell.

Another object of the invention is to provide improved establishment efficiency of a self-replicating non-integrative episomal S/MAR expression vector in a target vertebrate cell.

In one embodiment, the present technology provides a method for improving the expression and establishment efficiency of a self-replicating non-integrative episomal S/MAR expression vector in a target vertebrate cell comprising the following steps: a) providing a episomal S/MAR expression vector comprising: i) a bacterial replication-selection region comprising a bacterial origin of replication and a selectable marker; ii) a transcription unit for expression of a transgene in a vertebrate cell, comprising a promoter, a 5' UTR, a transgene, and a 3' UTR: iii) an S/MAR insert located within said 3' UTR; and b) modifying the episomal S/MAR expression vector such that the S/MAR is flanked by a 5' splice donor site and a 3' splice acceptor site within said 3' UTR, whereby the resultant self-replicating non-integrative episomal S/MAR expression vector has improved the expression and establishment efficiency after transfection of a vertebrate cell. In a further embodiment said S/MAR contains internal AATAAA transcription termination motifs. In a further embodiment said AATAAA transcription termination motifs in said S/MAR are replaced with AATATT motifs. In a further embodiment said S/MAR is selected from the group consisting of human Interferon beta S/MAR, M18 S/MAR, ApoL1 S/MAR. In a further embodiment said SMAR flanked by a 5' splice donor site and a 3' splice acceptor site has at least 95% sequence identity to a sequence selected from the group consisting of SEQ ID NO: 19, SEQ ID NO: 20, SEQ ID NO. 21, SEQ ID NO: 22, and SEQ ID NO: 23 In a further embodiment said bacterial origin of replication is an R6K gamma replication origin. In a further embodiment said bacterial origin of replication is an R6K gamma replication origin with at least 95% sequence identity to a sequence selected from the group consisting of SEQ ID NO: 1, SEQ ID NO: 2, SEQ ID NO: 3, and SEQ ID NO: 4. In a further embodiment said selectable marker is an RNA-1N regulating RNA-OUT functional variant with at least 95% sequence identity to a sequence selected from the group consisting of SEQ ID NO: 5, and SEQ ID NO: 7. In a further embodiment said selectable marker is an RNA-OUT RNA selectable marker that encodes an RNA-IN regulating RNA-OUT RNA with at least 95% sequence identity to SEQ ID NO: 6. In a further embodiment said bacterial replication-selection region comprising a bacterial origin of replication and a selectable marker is a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13. SEQ ID NO: 14, SEQ ID NO: 15, SEQ ID NO: 16, and SEQ U) NO: 17. In a further embodiment said 5' UTR further encodes an intron. In a further embodiment said transcription unit further encodes an expression enhancer positioned upstream of the promoter. In a further embodiment said expression enhancer has at least 95% sequence identity to a sequence selected from the group consisting of SEQ ID NO: 27, and SEQ ID NO. 28. In a further embodiment said splice donor site has at least 95% sequence identity to SEQ ID NO:25. In a further embodiment said splice acceptor site has at least 95% sequence identity to SEQ ID NO: 26. In a further embodiment said self-replicating non-integrative episomal S/MAR expression vector is selected from the group consisting of plasmid vector. Nanoplasmid vector. Mini-Intronic Plasmid, Integration-Deficient Lentivirus vector, and Non-integrating Lentiviral vectors.

In another embodiment, the present technology provides an antibiotic marker free covalently closed circular recombinant DNA molecule comprising, a) an antibiotic marker free transcription unit for expression of a transgene in a vertebrate cell, comprising a promoter, a 5' UTR, a transgene, and a 3' UTR; b) an S/MAR located within said 3' UTR wherein said S/MAR is flanked by a 5' splice donor site and a 3' splice acceptor site; c) an R6K gamma replication origin with at least 95% sequence identity to a sequence selected from the group consisting of SEQ ID NO: 1, SEQ ID NO: 2, SEQ ID NO: 3, and SEQ ID NO: 4; and d) an RNA-OUT RNA selectable marker comprising an RNA-IN regulating RNA-OUT functional variant with at least 95% sequence identity to a sequence selected from the group consisting of SEQ ID NO: 5, and SEQ ID NO: 7. In a further embodiment said R6K gamma replication origin and said RNA-OUT RNA selectable marker comprise a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15. SEQ ID NO: 16, and SEQ ID NO: 17. In a further embodiment said S/MAR is selected from the group consisting of human Interferon beta S/MAR, M18 S/MAR, ApoL1 S/MAR. In a further embodiment said S/MAR contains internal AATAAA transcription termination motifs. In a further embodiment said AATAAA transcription termination motifs in said S/MAR are replaced with AATATT motifs In a further embodiment said Si/MAR is selected from the group consisting of human Interferon beta S/MAR, M18 S/MAR, ApoL1 S/MAR. In a further embodiment said SMAR flanked by a 5' splice donor site and a 3' splice acceptor site has at least 95% sequence identity to a sequence selected from the group consisting of SEQ ID NO 19. SEQ ID NO: 20, SEQ ID NO: 21, SEQ ID NO: 22, and SEQ ID NO: 23. In a further embodiment said 5' UTR further encodes an intron. In a further embodiment said transcription unit further encodes an expression enhancer positioned upstream of the promoter. In a further embodiment said expression enhancer has at least 95% sequence identity to a sequence selected from the group consisting of SEQ ID NO: 27, and SEQ ID NO: 28. In a further embodiment said splice donor site has at least 95% sequence identity to SEQ ID NO:25. In a further embodiment said splice acceptor site has at least 95% sequence identity to SEQ ID NO: 26.

In another embodiment, the present technology provides an covalently closed circular recombinant DNA molecule comprising a) an transcription unit for expression of a transgene in a vertebrate cell, comprising a promoter, a 5' UTR, a transgene, and a 3' UTR, b) an S/MAR located within said 3' UTR wherein said S/MAR is flanked by a 5' splice donor site and a 3' splice acceptor site, c) an R6K gamma replication origin with at least 95% sequence identity to a sequence selected from the group consisting of SEQ ID NO: 1, SEQ ID NO. 2, SEQ ID NO: 3, and SEQ ID NO: 4, and d) an RNA-OUT RNA selectable marker comprising an RNA-IN regulating RNA-OUT functional variant with at least 95% sequence identity to a sequence selected from the group consisting of SEQ ID NO: 5, and SEQ ID NO 7. In a further embodiment said R6K gamma replication origin and said RNA-OUT RNA selectable marker comprise a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11. SEQ ID NO: 12, SEQ ID NO: 13, SEQ ID NO: 14, SEQ ID NO: 15, SEQ ID NO: 16, and SEQ ID NO: 17. In a further embodiment said S/MAR is selected from the group consisting of human Interferon beta S/MAR, M18 S/MAR, ApoL1 S/MAR. In a further embodiment said S/MAR contains internal AATAAA transcription termination motifs. In a further embodiment said AATAAA transcription termination motifs in said S/MAR are replaced with AATATT motifs In a further embodiment said S/MAR is selected from the group consisting of human Interferon beta S/MAR, M18 S/MAR, ApoL1 S/MAR. In a further embodiment said SMAR flanked by a 5' splice donor site and a 3' splice acceptor site has at least 95% sequence identity to a sequence selected from the group consisting of SEQ ID NO: 19, SEQ ID NO: 20, SEQ ID NO: 21, SEQ ID NO 22, and SEQ ID NO: 23. In a further embodiment said 5' UTR further encodes an intron. In a further embodiment said transcription unit further encodes an expression enhancer positioned upstream of the promoter. In a further embodiment said expression enhancer has at least 95% sequence identity to a sequence selected from the group consisting of SEQ ID NO: 27, and SEQ ID NO: 28. In a further embodiment said splice donor site has at least 95% sequence identity to SEQ ID NO:25. In a further embodiment said splice acceptor site has at least 95% sequence identity to SEQ ID NO: 26.

The resultant plasmids with a S/MAR flanked by a 5' splice donor site and a 3' splice acceptor site within the 3' UTR have surprisingly improved establishment and transgene expression than plasmids with a S/MAR within the 3' UTR without flanking splice donor and acceptor sites.

Further objects and advantages of the invention will become apparent from a consideration of the drawings and ensuing description.

Figure 1:
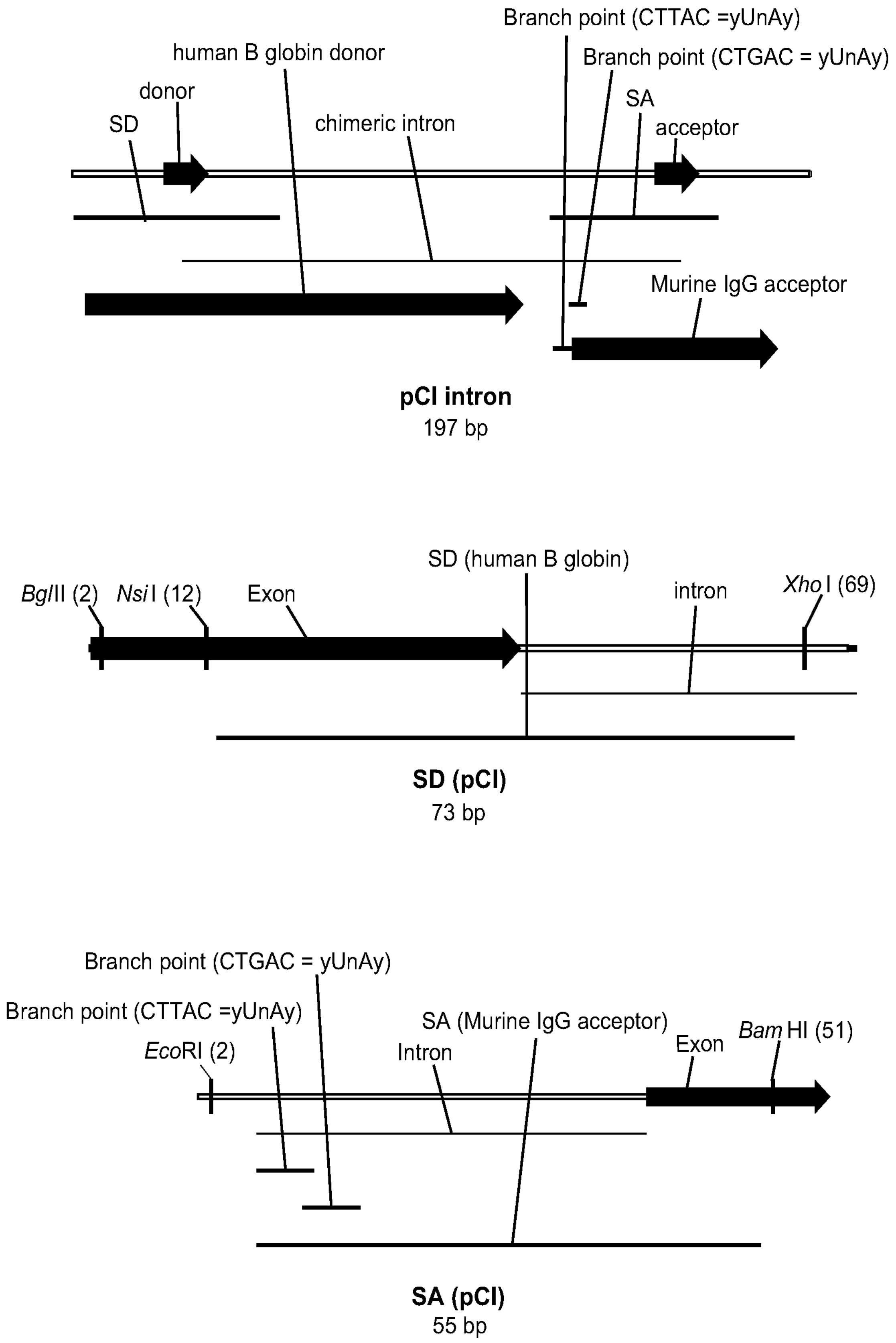
FIG. 1 depicts the pCI intron, with splice donor (SD) branch point and splice acceptor (SA) regions.

Table 1: pNTC multiple cloning site flanked R6K Origin-RNA-OUT selection marker vectors Table 2: Transient expression of S/MAR vectors after transfection into A549 and HEK293 cell lines Table 3: Transient expression of S/MAR vectors after transfection into A549 and HEK293 cell lines Table 4: Transient expression of S/MAR vectors after transfection into A549 and HEK293 cell lines SEQ ID NO:1: R6K gamma origin
SEQ ID NO:2: 1 CpG R6K gamma origin
SEQ ID NO:3: CpG free R6K gamma origin
SEQ ID NO:4: Extended R6K gamma origin
SEQ ID NO:5: RNA-OUT Selectable Marker
SEQ ID NO:6: RNA-OUT antisense repressor RNA
SEQ ID NO:7: 2 CpG RNA-OUT Selectable Marker
SEQ ID NO:8: R6K gamma origin-RNA-OUT bacterial region flanked by NheI and KpnI restriction sites
SEQ ID NO:9: 1 CpG R6K gamma origin-2 CpG RNA-OUT bacterial region flanked by NheI and KpnI restriction sites
SEQ ID NO:10: pNTC-NP1 polylinker trpA R6K-RNA-OUT polylinker cloning cassette: EcoRI/HindIII
SEQ ID NO:11: pNTC-NP2 polylinker trpA R6K-RNA-OUT polylinker cloning cassette: EcoRI/HindII
SEQ ID NO:12: pNTC-NP3 polylinker trpA R6K-RNA-OUT polylinker cloning cassette: EcoRI/HindIII
SEQ ID NO:13: pNTC-NP4 polylinker trpA R6K-RNA-OUT polylinker cloning cassette: EcoRI/HindII
SEQ ID NO: 14: pNTC-NP5 polylinker trpA R6K-RNA-OUT polylinker cloning cassette: KasI/HindIII
SEQ ID NO: 15: pNTC-NP6 polylinker trpA R6K-RNA-OUT polylinker cloning cassette: EcoRI/SacI
SEQ ID NO:16: pNTC-NP7 polylinker trpA R6K-RNA-OUT polylinker cloning cassette: BssHII/BssHII
SEQ ID NO: 17: pNTC-3×CpG NP1 polylinker R6K-RNA-OUT polylinker cloning cassette: HindIII/EcoR1
SEQ ID NO:18: Human Interferon beta S/MAR flanked by 5' BglII-XhoI site and 3' EcoRI restriction enzyme sites
SEQ ID NO:19: Splice donor-human Interferon beta S/MAR-splice acceptor flanked by 5' BglII site and 3' BamHI restriction enzyme sites
SEQ ID NO:20: Splice donor-human Interferon beta S/MAR (-AATAAA)-splice acceptor flanked by 5' BglII site and 3' BamHI restriction enzyme sites
SEQ ID NO:21: Splice donor-human Interferon beta M18 S/MAR-splice acceptor flanked by 5' BglII site and 3' BamHI restriction enzyme sites
SEQ ID NO:22: Splice donor-805 bp human Apolipoprotein B S/MAR-splice acceptor flanked by 5' BglII site and 3' BamHI restriction enzyme sites
SEQ ID NO:23: Splice donor-525 bp human Apolipoprotein B S/MAR-splice acceptor flanked by 5' NsiI site and 3' BamHI restriction enzyme sites
SEQ ID NO:24: pCI intron
SEQ ID NO:25: pCI Splice donor
SEQ ID NO:26: pCI Splice acceptor (murine IgG)
SEQ ID NO:27: Ele40 expression enhancer
SEQ ID NO:28: A2UCOE expression enhancer
SEQ ID NO:29: Splice acceptor consensus sequence

Definition of Terms

AF: Antibiotic-free
amp: Ampicillin
ampR: Ampicillin Resistance gene
Antibiotic selectable marker: A gene that confirs resistance to an antibiotic. e.g. ampicillin resistance gene, kanamycin resistance gene, chloramphenicol resistance gene, neomycin resistance gene, puromycin resistance gene, tetracycline resistance gene
ApoB: Apolipoprotein B
Approximately: As used herein, the term “approximately” or “about,” as applied to one or more values of interest, refers to a value that is the same or similar to a stated reference value
Bacterial region: Region of a plasmid vector required for propagation and selection in the bacterial host. The Bacterial region may be positioned within the spacer region in a plasmid or Nanoplasmid vector, or within an intron in a Mini-Intronic-Plasmid vector
bp: basepairs
ccc: Covalently Closed Circular
cI: Lambda repressor
cITs857: Lambda repressor further incorporating a C to T (Ala to Thr) mutation that confers temperature sensitivity, cITs857 is a functional repressor at 28-30° C. but is mostly inactive at 37-42° C. Also called cI857
$Cat^R$: Chloramphenicol resistance gene cmv: Cytomegalovirus

*E. coli: Escherichia coli*, a gram negative bacteria

EGFP: Enhanced green fluorescent protein

ELE40: anti-repressor element Element 40, STAR40 disclosed in Kwaks et al, 2003, *Nat Biotechnol.* 21:553

EP: Electroporation

Establishment efficiency: The percentage of cells in which a self-replicating non-integrative episomal S/MAR expression vector is stably retained as a replicative episome after transfection Eukaryotic expression vector: A vector for expression of mRNA, protein antigens, protein therapeutics, shRNA, RNA or microRNA genes in a target eukaryotic cell or organism using RNA Polymerase I, II or III promoters Eukaryotic region: The region of a plasmid that encodes eukaryotic sequences and/or sequences required for plasmid function in the target organism. This includes the region of a plasmid vector required for expression of one or more transgenes in the target organism including RNA Pol II enhancers, promoters, transgenes and polyA sequences. This also includes the region of a plasmid vector required for expression of one or more transgenes in the target organism using RNA Pol I or RNA Pol III promoters, RNA Pol I or RNA Pol III expressed transgenes or RNAs. The eukaryotic region may optionally include other functional sequences, such as eukaryotic transcriptional terminators, supercoiling-induced DNA duplex destabilized (SIDD) structures, S/MARs, boundary elements, etc.

Exon: A nucleotide sequence encoded by a gene that is transcribed and present within a mature mRNA product after RNA splicing to remove introns has been completed Expression enhancer: A DNA sequence that improves the expression of an adjacent promoter For example, Ele40, UCOE, anti-repressor elements, or Stabilising Anti Repressor (STAR) elements as reviewed in Saunders et al., 2015 PloS One 10:e0120096

Expression vector: A vector for expression of mRNA, protein antigens, protein therapeutics, shRNA, RNA or microRNA genes in a target organism g: Gram, kg for kilogram gene of interest: gene to be expressed in the target organism. Includes mRNA genes that encode protein or peptide antigens, protein or peptide therapeutics, and mRNA, shRNA, RNA or microRNA that encode RNA therapeutics, and mRNA, shRNA, RNA or microRNA that encode RNA vaccines, etc.

GFP: Green fluorescent protein

Hr(s): Hour(s)

immune response: Antigen reactive cellular (e.g. antigen reactive T cells) or antibody (e.g. antigen reactive IgG) responses Intron: A nucleotide sequence encoded by a gene that is transcribed and subsequently removed from a mature mRNA product by RNA splicing between the 5' splice donor and 3' splice acceptor sites kan: Kanamycin kanR: Kanamycin Resistance gene kozak sequence: Optimized consensus DNA sequence gccRccATG (R=G or A) immediately upstream of an ATG start codon that ensures efficient translation initiation.

Lentiviral vector: Integrative viral vector that can infect dividing and non-dividing cells. Also call Lentiviral transfer plasmid. Plasmid encodes Lentiviral LTR flanked expression unit. Transfer plasmid is transfected into production cells along with Lentiviral envelope and packaging plasmids required to make viral particles MFI: Medium Fluorescent intensity Minicircle: Covalently closed circular plasmid derivatives in which the bacterial region has been removed from the parent plasmid by in vivo or in vitro site-specific recombination or in vitro restriction digestion/ligation. Minicircle vectors are replication incompetent in bacterial cells Mini-Intronic Plasmid: MIP vector, in which the bacterial region is encoded within an intron rather than the spacer region as described in Lu et al., 2013, *Mol. Ther* 21:954 mRNA: Messenger RNA

NA: Not Applicable

Nanoplasmid™ vector: Nanoplasmid Vector, a vector with a bacterial region combining an RNA selectable marker with a R6K, ColE2 or ColE2 related replication origin. For example, NTC938SC, NTC9685C, NTC9385R, NTC968SR vectors and modifications described in Williams, 2014 DNA plasmids with improved expression. World Patent Application WO2014035457

NeoR: neomycin resistance gene

Non-integrating lentiviral vector: A lentiviral vector with mutated integrase and a S/MAR for maintenance of episomal LTR circles such as those described in Verghese et al., 2014 *Nucleic Acids Research* 42:e53.

NP: Nanoplasmid

NTC8385: NTC8385 (and NTC8485 and NTC8685) plasmids are antibiotic-free pUC origin vectors that contain a short RNA (RNA-OUT) selectable marker instead of an antibiotic resistance marker such as kanR. The creation and application of these RNA-OUT based antibiotic-free vectors are described in Williams. JA 2008 World Patent Application WO2008 153733 and Williams, J A 2010 US Patent Application 20100184158

NTC9385R: The NTC9385R Nanoplasmid™ vector described in Williams, Supra. 2014 has a spacer region encoded NheI-trpA terminator-R6K origin RNA-OUT-KpnI bacterial region (SEQ ID NO:8) linked through the flanking NheI and KpnI sites to the eukaryotic region $OD_{600}$: optical density at 600 nm PCR: Polymerase Chain Reaction pINT pR pL vector: The pINT pR pL $att_{HK022}$ integration expression vector is described in Luke et al., 2011 *Mol Biotechnol* 47.43. The target gene to be expressed is cloned downstream of the pL promoter. The vector encodes the temperature inducible cI857 repressor, allowing heat inducible target gene expression $P_L$ promoter: Lambda promoter left $P_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues $P_L$ (OL1 G to T) promoter: Lambda promoter left. $P_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues. The cI repressor binding to OL1 is reduced by the OL1 G to T mutation resulting in increased promoter activity at 30° C. and 37-42° C. as described in Williams. Supra, 2014.

Plasmid: An extra chromosomal DNA molecule separate from the chromosomal DNA which is capable of replicating independently from the chromosomal DNA Plasmid copy number: the number of copies of a plasmid per cell. Increases in plasmid copy number increase plasmid production yield Pol: Polymerase polyA: Polyadenylation signal or site. Polyadenylation is the addition of a poly(A) tail to an RNA molecule. The polyadenylation signal contains the sequence motif recognized by the RNA cleavage complex. Most human polyadenylation signals contain an AATAAA motif and conserved sequences 5' and 3' to it. Commonly utilized polyA signals are derived from the rabbit β globin (RBG), bovine growth hormone (BGH), SV40 early, or SV40 late polyA signals pUC origin: pBR322-derived replication origin, with G to A transition that increases copy number at elevated temperature and deletion of the ROP negative regulator pUC free: Plasmid that does not contain the pUC origin. Non-replicative fragments of the pUC origin may be included, for example the RNAI selectable marker pUC plasmid: Plasmid containing the pUC origin PuroR: Puromycin Resistance gene R6K plasmid: NTC9385R, NTC9685R, NTC9385R2-O1, NTC9385R2-O2, NTC9385R2a-O1, NTC9385R2a-O2, NTC9385R2b-O1, NTC9385R2b-O2, NTC9385Ra-O1, NTC9385Ra-O2, NTC9385RaF, and NTC9385RbF vectors as well as modifications and alternative vectors containing a R6K replication origin that were described in Williams, Supra, 2014. Alternative R6K vectors known in the art including, but not limited to, pCOR vectors (Gencell), pCpGfre vectors (Invivogen), and CpG free University of Oxford vectors including pGM169.

R6K replication origin: a region which is specifically recognized by the R6K Rep protein to initiate DNA replication. Includes but not limited to R6K gamma replication origin sequence disclosed as SEQ ID NO: 1, SEQ ID NO:2 and SEQ ID NO:4, and CpG free versions (e.g. SEQ ID NO:3) as described in Drocourt et al., U.S. Pat. No. 7,244,609

R6K replication origin-RNA-OUT bacterial region: Contains a R6K replication origin for propagation and the RNA-OUT selectable marker (e.g. SEQ ID NO:8: SEQ ID NO:9; SEQ ID NO: 10; SEQ ID NO: 11; SEQ ID NO: 12; SEQ ID NO:13; SEQ ID NO:14; SEQ ID NO: 15; SEQ ID NO: 16: SEQ ID NO:17). Bacterial region may be encoded in the spacer region (Nanoplasmid vector) or in an intron (Mini-Intronic-Plasmid vector)

Rep: Replication

Rep protein dependent plasmid: A plasmid in which replication is dependent on a replication (Rep) protein provided in Trans. For example, R6K replication origin, ColE2-P9 replication origin and ColE2 related replication origin plasmids in which the Rep protein is expressed from the host strain genome. Numerous additional Rep protein dependent plasmids are known in the art, many of which are summarized in del Solar et al., Supra, 1998

Retroviral vector: Integrative viral vector that can infect dividing cells. Also call transfer plasmid. Plasmid encodes Retroviral LTR flanked expression unit. Transfer plasmid is transfected into production cells along with envelope and packaging plasmids required to make viral particles RNA-IN: Insertion sequence 10 (IS 10) encoded RNA-IN, an RNA complementary and antisense to a portion of RNA RNA-OUT. When RNA-IN is cloned in the untranslated leader of a mRNA, annealing of RNA-IN to RNA-OUT reduces translation of the gene encoded downstream of RNA-IN RNA-IN regulated selectable marker: A chromosomally expressed RNA-IN regulated selectable marker. In the presence of plasmid borne RNA-OUT antisense repressor RNA (SEQ ID NO:6), expression of a protein encoded downstream of RNA-IN is repressed. An RNA-IN regulated selectable marker is configured such that RNA-IN regulates either 1) a protein that is lethal or toxic to said cell per sc or ht generating a toxic substance (e.g. SacB), or 2) a repressor protein that is lethal or toxic to said bacterial cell by repressing the transcription of a gene that is essential for growth of said cell (e.g. murA essential gene regulated by RNA-IN tetR repressor gene). For example, chromosomally expressed RNA-IN-SacB cell lines for RNA-OUT plasmid selection propagation are described in Williams, Supra. 2008. Alternative selection markers described in the art may be substituted for SacB RNA-OUT: Insertion sequence 10 (IS 10) encoded RNA-OUT, an antisense RNA that hybridizes to, and reduces translation of, the transposon gene expressed downstream of RNA-IN. The sequence of the RNA-OUT RNA (SEQ ID NO:6) and complementary RNA-IN SacB chromosomally expressed RNA-IN-SacB cell lines can be modified to incorporate alternative functional RNA-IN/RNA-OUT binding pairs such as those described in Mutalik et al. 2012 *Nat Chem Biol* 8:447, including, but not limited to, the RNA-OUT A08/RNA-IN S49 pair, the RNA-OUT A08/RNA-IN S08 pair, and CpG free modifications of RNA-OUT A08 that modify the CG in the RNA-OUT 5' TTCQC sequence to a non-CpG sequence. An example of a CpG free RNA-OUT selection marker, in which the two CpG motifs in the RNA-OUT RNA (one of which is present in the RNA-IN complementary region) are removed, was described in Williams 2015. Replicative minicircle vectors with improved expression. US Patent Application US 2015/0275221. A multitude of alternative substitutions to remove the two CpG motifs (mutating each CpG to either CpA, CpC, CpT, ApG, GpG, or TpG) may be utilized to make a CpG free RNA-OUT RNA-OUT Selectable marker: An RNA-OUT selectable marker DNA fragment including *E. coli* transcription promoter and terminator sequences flanking an RNA-OUT RNA. An RNA-OUT selectable marker, utilizing the RNA-OUT promoter and terminator sequences, that is flanked by DraIII and KpnI restriction enzyme sites, and designer chromosomally expressed RNA-IN-SacB cell lines for RNA-OUT plasmid propagation, are described in Williams, Supra. 2008. The RNA-OUT promoter and terminator sequences in SEQ ID NO: 5 that flank the RNA-OUT RNA (SEQ ID NO:6) may be replaced with heterologous promoter and terminator sequences. For example, the RNA-OUT promoter may be substituted with a CpG free promoter known in the art, for example the I-EC2K promoter or the P5/6 5/6 or P5/6 6/6 promoters described in Williams, Supra. 2008. A 2 CpG RNA-OUT selectable marker in which the two CpG motifs in the RNA-OUT promoter are removed is given as SEQ ID NO 7. An example of a CpG free RNA-OUT transcription unit, in which the two CpG motifs in the RNA-OUT RNA (one of which is present in the RNA-IN complementary region) and the two CpG motifs in the RNA-OUT promoter are removed was described in Williams, Supra, 2015. Vectors incorporating CpG free RNA-OUT selectable marker may be selected for sucrose resistance using the RNA-IN-SacB cell lines for RNA-OUT plasmid propagation described in Williams, Supra, 2008. Alternatively, the RNA-IN sequence in these cell lines can be modified to incorporate the 1 bp change needed to perfectly match the CpG free RNA-OUT region complementary to RNA-IN RNA polymerase II promoter: Promoter that recruits RNA Polymerase 11 to synthesize mRNAs, most small nuclear RNAs and microRNAs. For example, constitutive promoters such as the human or murine CMV promoter, elongation factor 1 (EF1) promoter, the chicken β-actin promoter, the β-actin promoter from other species, the elongation factor-1 α (EF1 α) promoter, the phosphoglycerokinase (PGK) promoter, the Rous sarcoma virus (RSV) promoter, the human serum albumin (SA) promoter, the spleen focus-forming virus (SFFV) promoter, the α-1 antitrypsin (AAT) promoter, the thy oxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EF1α) promoters. CpG free versions of the human or murine CMV-derived enhancer elements combined with the elongation factor 1α (EF1α) promoters, the albumin promoter combined with an α-fetoprotein MERII enhancer, etc., or the diversity of tissue specific or inducible promoters know in the art such as the muscle specific promoters muscle creatine kinase (MCK), and CS-12 or the liver-specific promoters ApoE-hAAT, apolipoprotein A-1 (ApoA1), etc.

RNA polymerase III promoter: Promoter that recruits RNA Polymerase III to synthesize tRNAs, 5S ribosomal RNA, and other small RNAs. For example, Class I promoters such as the 5s rRNA promoter, Class II promoter such as tRNA promoters. Class III promoters such as the U6 small nuclear RNA promoter or the H1 nuclear RNase P promoter, etc.

RNA selectable marker: An RNA selectable marker is a plasmid borne expressed non-translated RNA that regulates a chromosomally expressed target gene to afford selection. This may be a plasmid borne nonsense suppressing tRNA that regulates a nonsense suppressible selectable chromosomal target as described by Crouzet J and Soubrier F 2005 U.S. Pat. No. 6,977,174. This may also be a plasmid borne antisense repressor RNA, a non limiting list included herein includes RNA-OUT that represses RNA-IN regulated targets (Williams, Supra. 2008), pMB1 plasmid origin encoded RNAI that represses RNAII regulated targets (Grabherr R, Pfaffieneller I. 2006 US patent application US20060063232; Cranenburgh R M. 2009; U.S. Pat. No. 7,611,883), IncB plasmid pMU720 origin encoded RNAI that represses RNA II regulated targets (Wilson I W, Siemering K R, Praszkier J. Pittard A J. 1997. *J Bacteriol* 179:742-53). ParB locus Sok of plasmid R1 that represses Hok regulated targets, Flm locus FlmB of F plasmid that represses flmA regulated targets (Morsey M A, 1999 U.S. Pat. No. 5,922,583). An RNA selectable marker may be another natural antisense repressor RNAs known in the art such as those described in Wagner EGH. Altuvia S, Romby P. 2002. *Adv Genet* 46:361-98 and Franch T, and Gerdes K. 2000. *Current Opin Microbiol* 3:159-64. An RNA selectable marker may also be an engineered repressor RNAs such as synthetic small RNAs expressed SgrS, MicC or MicF scaffolds as described in Na D, Yoo S M, Chung H, Park H, Park J H, Lee S Y. 2013. *Nat Biotechnol* 31:170-4. An RNA selectable marker may also be an engineered repressor RNA as part of a selectable marker that represses a target RNA fused to a target gene to be regulated such as SacB as described in Williams, Supra, 2015

ROP: Repressor of primer

RSM: RNA selectable marker

SA: Splice Acceptor, consensus sequence YYYYYYYYYYYAGRW is presented as SEQ ID NO:29. To create an effective SA site, a splice branch point (consensus sequence YTNAY) is included upstream of the splice acceptor site (see FIG. 1).

SacB: Structural gene encoding *Bacillus subtilis* levansucrase. Expression of SacB in gram negative bacteria is toxic in the presence of sucrose SD: Splice Donor, consensus sequence AGGTRAGT SEAP: Secreted alkaline phosphatase Selectable marker. A selectable marker, for example a kanamycin resistance gene or an RNA selectable marker Selection marker: A selectable marker, for example a kanamycin resistance gene or an RNA selectable marker SIDD: supercoiling-induced DNA duplex destabilized (SIDD) structures. These sites, when incorporated into a vector, may alter the susceptibility of other sequences within the vector to be destabilized. This can alter function. For example, addition of a SIDD site to an expression vector may reduce the helical destabilization of a promoter. This may increase or decrease promoter activity, depending on the promoter since some promoters have increased expression with promoter helical destabilization, while others will have reduced expression with promoter helical destabilization shRNA: Short hairpin RNA S/MAR: Scaffold/matrix attachment region. Eukaryotic sequences that mediate DNA attachment to the nuclear matrix Spacer region: As used herein, spacer region is the region linking the 5' and 3' ends of the eukaryotic region sequences. The eukaryotic region 5' and 3' ends are typically separated by the bacterial replication origin and bacterial selectable marker in plasmid vectors.

SR: Spacer region.

target antigen: Immunogenic protein or peptide epitope, or combination of proteins and epitopes, against which an immune response can be mounted. Target antigens may by derived from a pathogen for infectious disease or allergy applications or derived from a host organism for applications such as cancer, allergy, or autoimmune diseases. Target antigens are well defined in the art. Some examples are described in Williams, Supra. 2008

TE buffer: A solution containing approximately 10 mM Tris pH 8 and 1 mM EDTA

TetR: Tetracycline resistance gene

Transcription termination motif: AATAAA. Internal cleavage at AATAAA sites leaves an uncapped 5'end on the 3UTR RNA for nuclease digestion. Nuclease catches up to RNA Pol II and causes termination.

transfection: Method to deliver nucleic acids into cells [e.g. poly(lactide-co-glycolide) (PLGA), ISCOMs, liposomes, niosomes, virosomes, chitosan, and other biodegradable polymers, microparticles, microspheres, nanoparticles, nanocapsules, electroporation, nucleofection, piezoelectric permeabilization, sonoporation, iontophoresis, ultrasound, SQZ high speed cell deformation mediated membrane disruption, corona plasma, plasma facilitated delivery tissue tolerable plasma, laser microporation, shock wave energy, magnetic fields, contactless magneto-permeabilization, gene gun, microneedles, microdermabrasion, hydrodynamic delivery, high pressure tail vein injection, etc] as known in the art Transgene: Gene of interest that is cloned into a vector for expression in a target organism ts: Temperature sensitive μg: Microgram μl: Microliter UCOE: Ubiquitous Chromatin Opening Element, such as the A2UCOE or minimal derivatives as disclosed in Muller-Kuller et al., 2015, *Nucleic Acids Research* 43:1577

UTR: Untranslated region of a mRNA (5' or 3' to the coding region)

Vector: A gene delivery vehicle, including viral (e.g. Alphavirus, Poxvirus, Lentivirus, Retrovirus. Adenovirus, Adenovirus related virus, Integration-Deficient Lentiviral vectors, etc.) and non-viral (e.g. plasmid, Nanoplasmid, Mini-Intronic-Plasmid, MIDGE, transcriptionally active PCR fragment, minicircles, bacteriophage, etc.) vectors. These are well known in the art Vector backbone: Eukaryotic region and bacterial region of a vector, without the transgene or target antigen coding region Vertebrate expression vector: A vector for expression of mRNA, protein antigens, protein therapeutics, shRNA, RNA or microRNA genes in a target vertebrate cell or organism using RNA Polymerase I, II or III promoters

DETAILED DESCRIPTION OF THE PREFERRED EMBODIMENTS

The current technology relates generally to self-replicating non-integrative episomal vertebrate expression vector methods and compositions that improve episomal replication and transgene expression. The current technology can be practiced to improve expression and episomal replication of vectors such as non-viral vectors and viral vectors (e.g. episomal integration-Deficient Lentivirus vector. Non-integrating Lentiviral vectors, episomal Retroviral vector, etc.).

Improved episomal replication is defined herein as improved non-integrative episomal vector establishment and/or maintenance in vitro or in vivo compared to a vector that does not incorporate the current technology. Improved vector expression is defined herein as improved transgene expression level and/or expression duration in vitro or in vivo compared to a transgene encoding vector that does not incorporate the current technology. It is to be understood that all references cited herein are incorporated by reference in their entirety.

The methods of vector modification of the present current technology have been surprisingly found to provide a solution to provide self-replicating non-integrative episomal vectors with efficient establishment.

The vector methods and compositions disclosed herein are 3' UTR SD-SMAR-SA compositions with improved expression and or episomal establishment (improved performance) compared to non SD-SA versions. Improved performance is not S/MAR specific since performance improvement is observed with various S/MARs. Improved performance is also not vector transcription unit specific, since performance improvement is observed with SD-SMAR-SA linked to various promoters, 5' UTRs, transgenes, and polyA signals. Improved performance is observed with or without upstream introns. Improved performance is also observed with S/MAR's that contain transcription termination motifs. Improved performance is also observed with S/MAR's in which transcription termination is within the S/MAR. Thus, the 3' UTR SD-SMAR-SA vectors of the disclosure are broadly applicable to improve self-replicating non-integrative episomal vertebrate expression vector performance.

Figure 2:
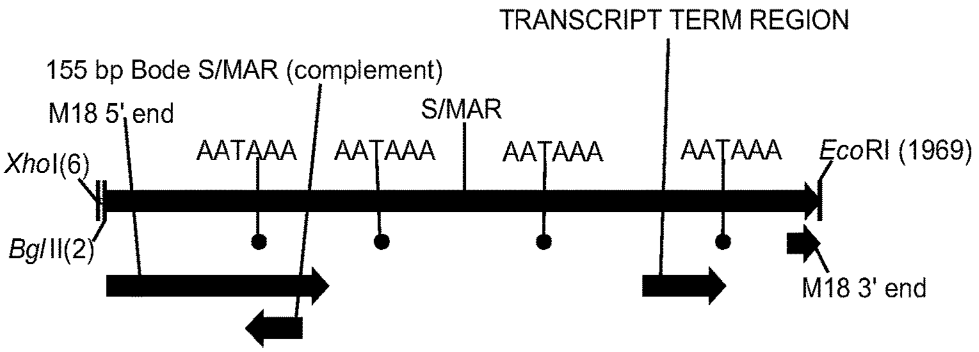
FIG. 2 depicts the interferon beta S/MAR (top), and a SD interferon beta S/MAR SA derivative (middle), as well as a SD interferon beta S/MAR SA derivative in which the internal AATAAA (N) polyadenylation signals were mutated to AATATTT (bottom). One of these polyadenylation signals is within the S/MAR internal transcription termination region identified by Stehle et al, 2003, Chromosome Research 11, 431
Figure 2:
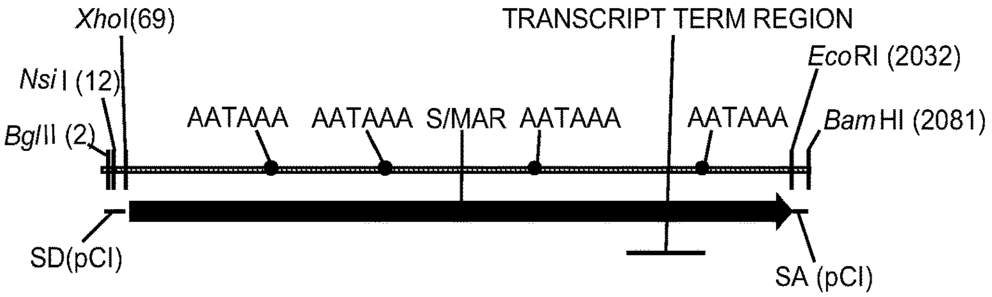
Figure 2:
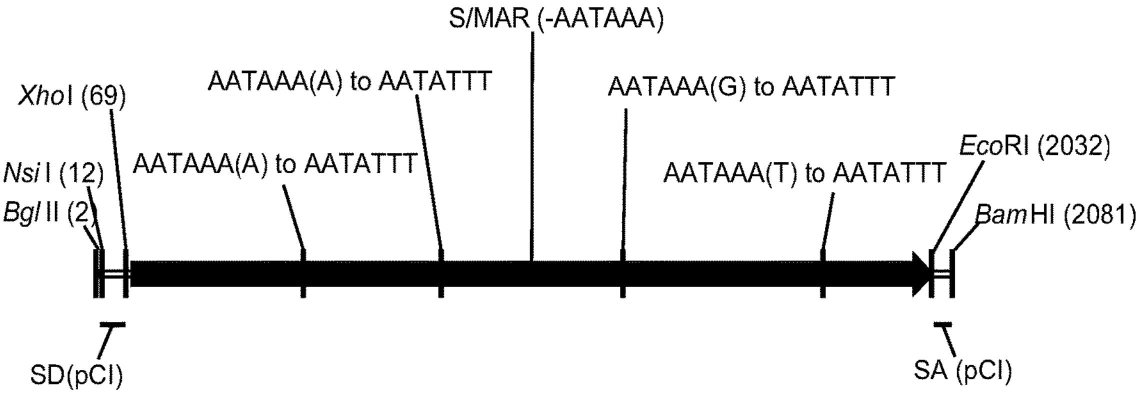

The disclosed improved performance of 3' UTR SD-SMAR-SA compared to non SD-SA versions is surprising in light of the prior art. For example, Le Hir et al., 2003 *Trends in Biochemical Sciences* 28:215 teaches 'Matsumoto et al. [51] found these translational effects to be highly dependent on intron position. In their study an intron placed in the 5' UTR was highly stimulatory, whereas the same intron placed in the 3'UTR repressed translation to below the level of the corresponding intronless mRNA.' . . . 'Nonetheless, for researchers interested in optimizing the expression of trangenes, it is important to note that intron position is an important variable. In addition to potentially inhibiting translation, introns in the 3' UTR can trigger nonsense-mediated decay (NMD) of the mRNA as described below, resulting in even lower protein expression.' Barrett et al., 2012 *Cell. Mol. Life Si.* 69:3613 teaches 'In contrast to 5'UTRs, 3'UTRs were found to have relatively few introns (5%) [21]. A study looking at rare cases of intron acquisition in retroposed mammalian genes found that the presence of an intron in the 3'UTR of these genes resulted in down-regulation of gene expression by nonsense-mediated decay [52]. This negative effect on expression offers an explanation for the low prevalence of 3'UTR intros.' The improved performance with an S/MAR that contains transcription termination motifs and demonstrated transcription termination internal to the S/MAR (human interferon beta S/MAR; FIG. 2. Stehle et al. Supra, 2003) teaches that the mechanism for improved performance cannot be simply splicing, since the results with the unmodified S/MAR predict that there would be no transcription of the splice acceptor site due to S/MAR internal transcription termination. While not limiting the application of the invention, adding flanking splice donor and splice acceptor splice sites may have an unexpected benefit to enhance transcription rate or progressivity in the disclosed invention in which the 3' UTR encodes an S/MAR sequence.

As used herein, the term "sequence identity" refers to the degree of identity between any given query sequence, e.g. SEQ ID NO: 2, and a subject sequence. A subject sequence may, for example, have at least 90 percent, at least 95 percent, or at least 99 percent sequence identity to a given query sequence. To determine percent sequence identity, a query sequence (e.g. a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., 2003 *Nucleic Acids Res.* 31:3497-500 In a preferred method, the sequence alignment program (e g ClustalW) calculates the best match between a query and one or more subject sequences, and aligns them so that identities, similarities, and differences can be determined. Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Turning now to the drawings, FIG. 1. shows annotated maps of the pCI intron (top), splice donor (SD) region (middle) and branch point and splice acceptor (SA) region (bottom).

FIG. Z shows annotated maps of the interferon beta S/MAR (top), and a SD interferon beta S/MAR SA derivative (middle), as well as a SD interferon beta S/MAR SA derivative in which the internal AATAAA (N) polyadenylation signals were mutated to AATATTT (bottom). One of these polyadenylation signals is within the S/MAR internal transcription termination region identified by Stehle et al, Supra, 2003

Figure 3:
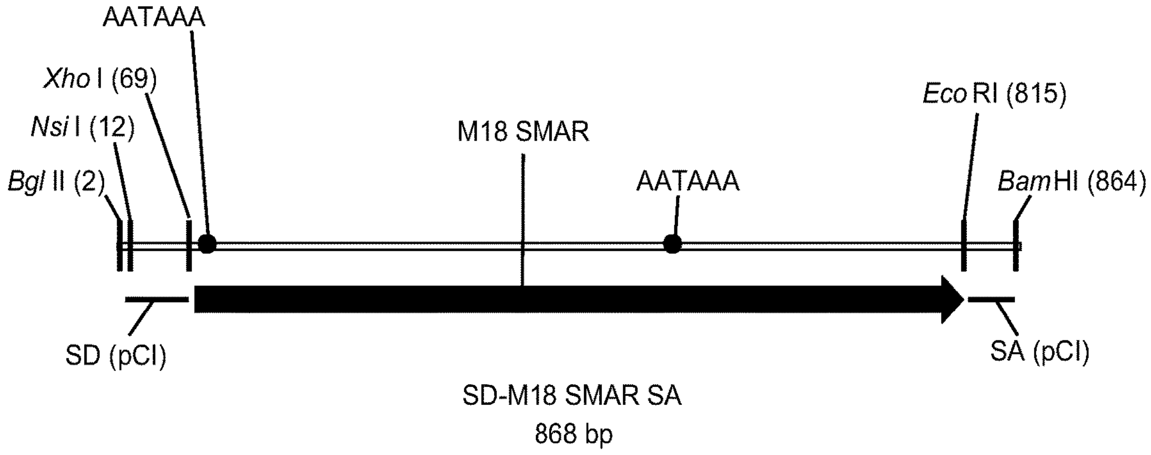
FIG. 3 depicts the interferon beta S/MAR derivative M18 with flanking SD and SA sites
Figure 4:
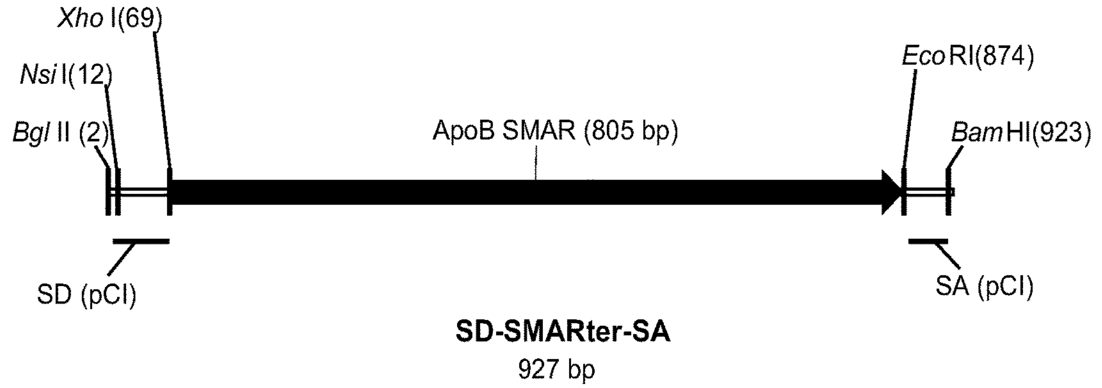
FIG. 4 depicts the 805 bp (top) or 525 bp (bottom) apoB S/MAR with flanking SD and SA sites
Figure 4:
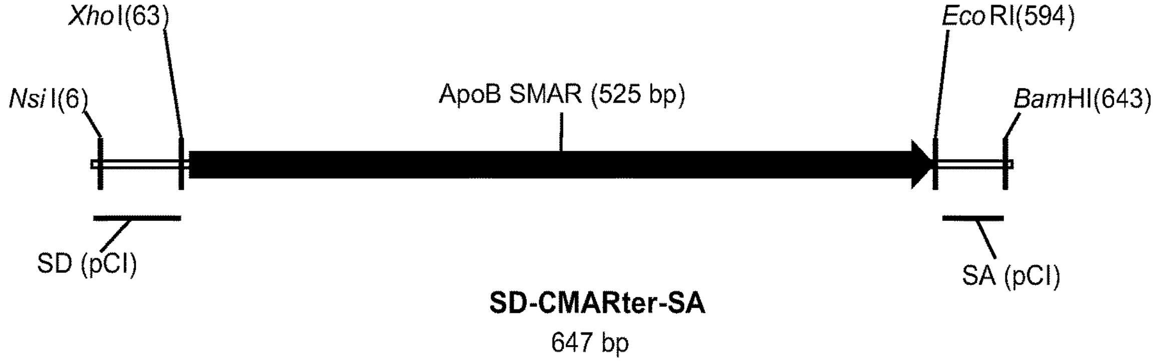
Figure 5:
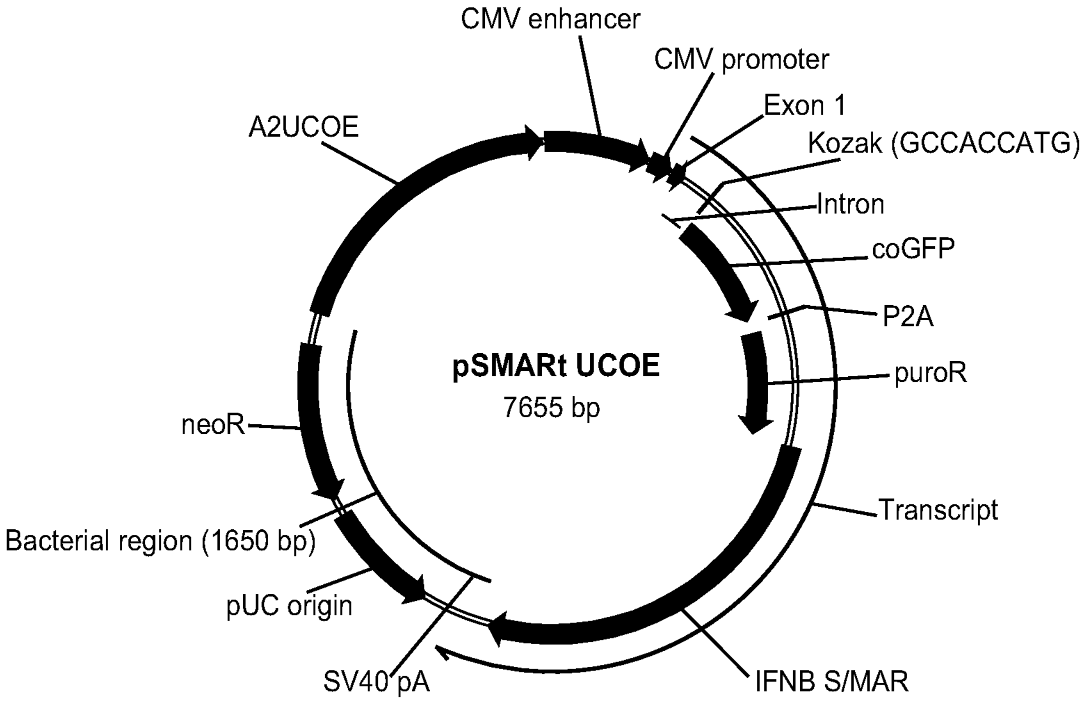
FIG. 5 depicts the pMAX-UCOE-coGFP P2A-PuroR-NP (pSMARt UCOE) vector
Figure 6:
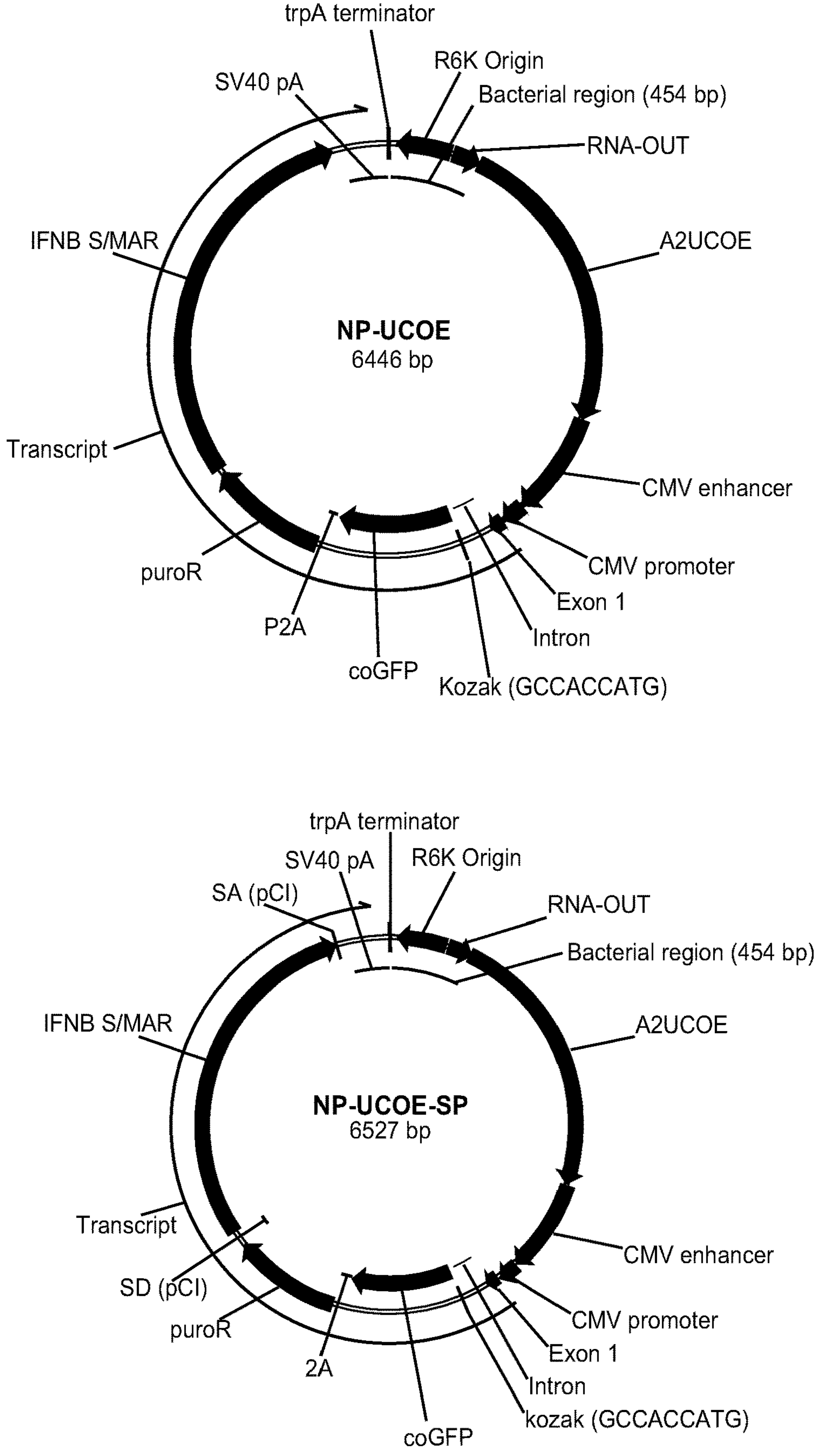
FIG. 6 depicts the NTC9385R-UCOE-CMV-coGFP P2A-PuroR-SMAR-SV40 pA (NP-UCOE) and NTC938SR-UCOE-CMV-coGFP P2A-PuroR-SD SMAR-SA SV40 pA (NP-UCOE-SP) vectors
Figure 7:
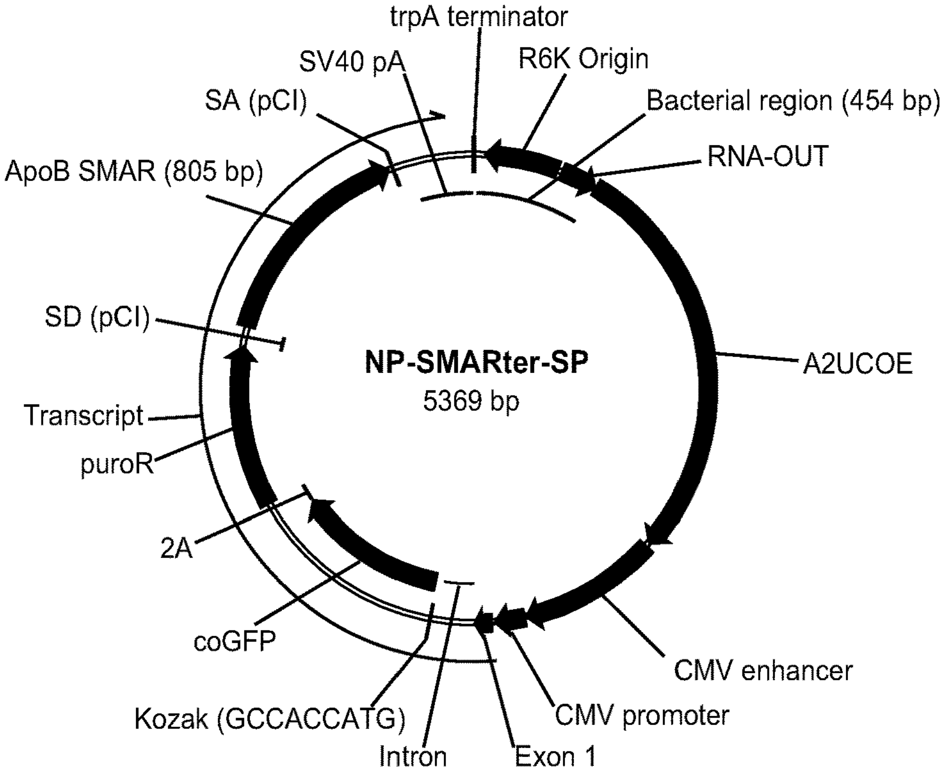
FIG. 7 depicts the NTC9383R-SP-UCOE-CMV-GFP SMARter (NP-SMARter-SP) and NTC9385R-SP-UCOE-CMV-GFP CMARter (NP-CMARter-SP) vectors
Figure 7:
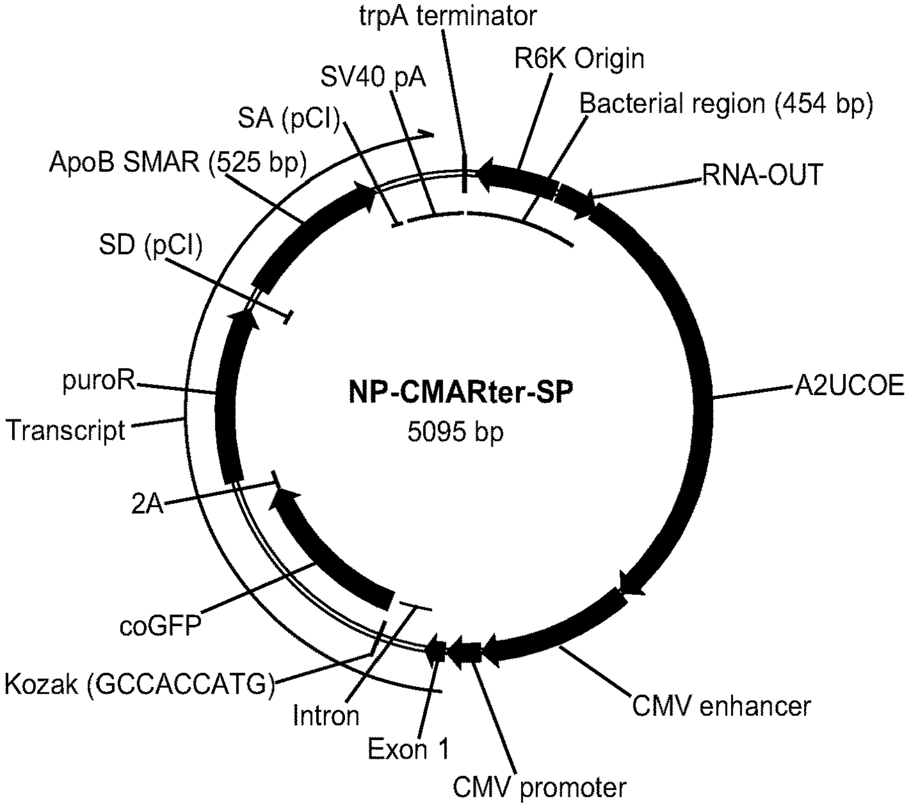
Figure 8:
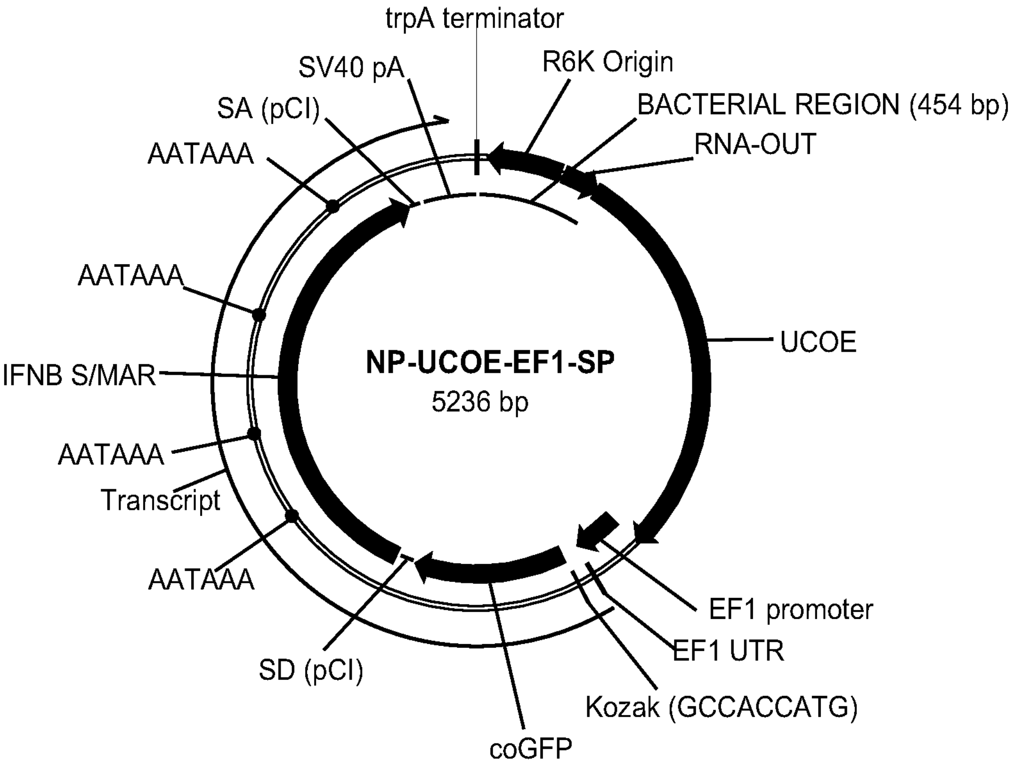
FIG. 8 depicts the NTC938SR-UCOE EF1-coGFP SD-SMAR SA SV40 pA (NP-UCOE-EF1-SP) and NTC9385R-UCOE EF1-coGFP-SD SMAR R6K-R-OUT-SA pA (UCOE-EF1-SP-NP) vectors
Figure 8:
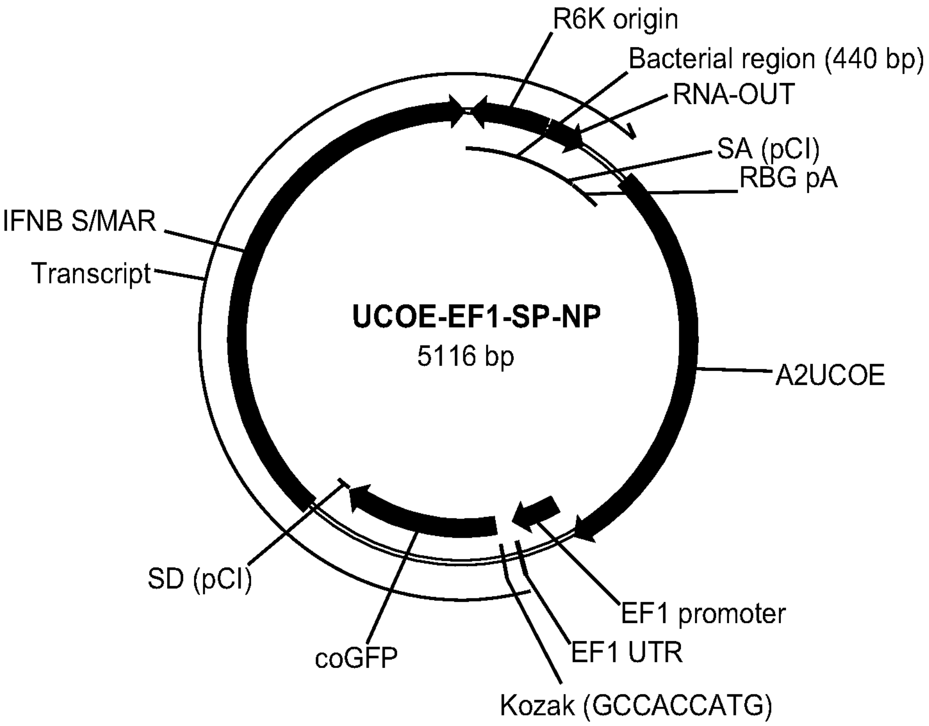
Figure 9:
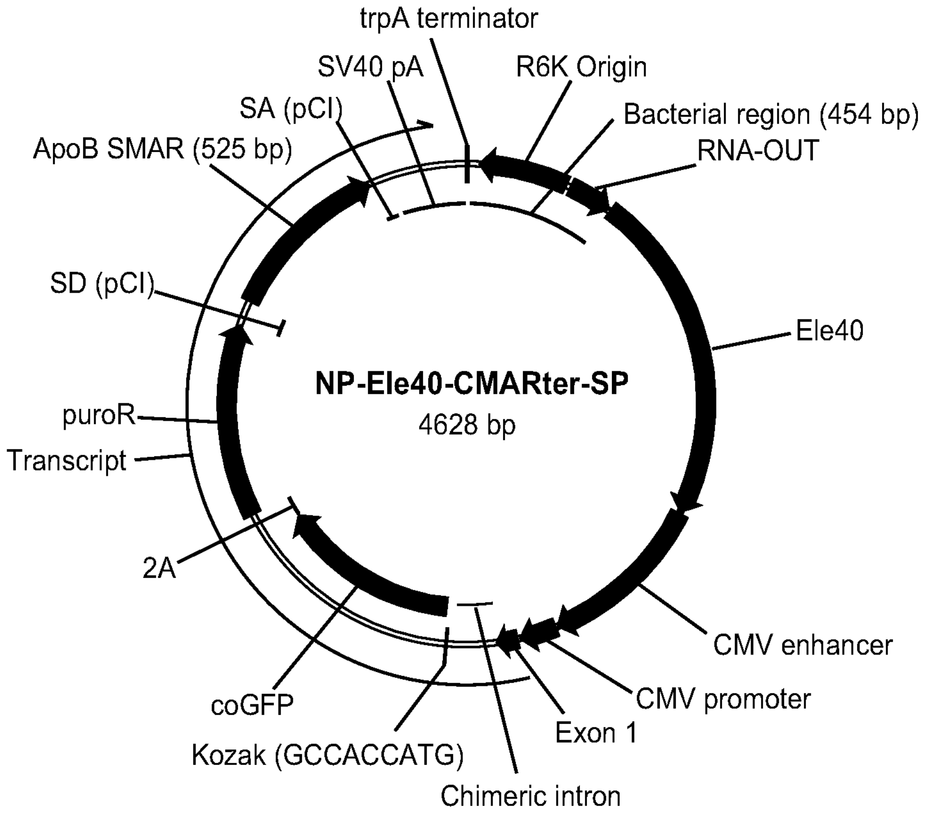
FIG. 9 depicts the NTC9385R-SP-ELE40-CMV-GFP CMARter (NP-Ele40-CMARter-SP) vector
Figure 10:
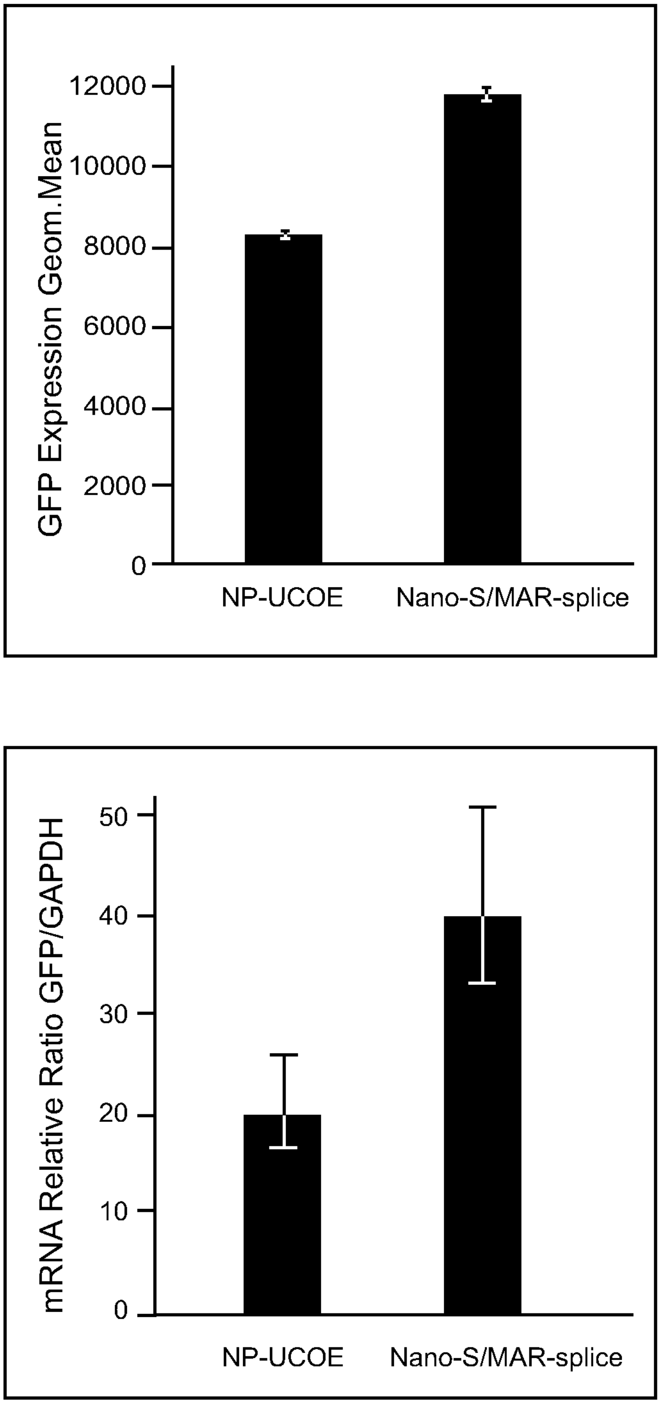
FIG. 10 depicts improved expression of established S/MAR vectors with flanking SD and SA sites. Left panel: MFI of HEK293T cells established with a S/MAR vector with and without splice junctions. The vectors contain NP bacterial region, the genomic insulator UCOE, the expression cassette GFP-2A-PuroR driven by the CMV promoter and the interferon beta S/MAR in the 3' UTR with (Nano-S/MAR-splice=NP-UCOE-SP; NTC9385R-UCOE-CMV-coGFP P2A-PuroR-SD SMAR-SA SV40 pA FIG. 6) or without (NP-UCOE: NTC9385R-UCOE-CMV-coGFP P2A-PuroR-SMAR-SV40 pA, FIG. 6) S/MAR flanking SD and SA sites. Right panel: the improved transcription expression is confirmed by real time PCR analysis. The expression of the transgene GFP was normalized to the housekeeping gene GAPDH.

FIG. 3 shows annotated maps of the interferon beta S/MAR derivative M18 with flanking SD and SA sites FIG. 4 shows annotated maps of the 805 bp (top) or 525 bp (bottom) apoB S/MAR with flanking SD and SA sites FIG. 5 shows an annotated map of the pMAX-UCOE-coGFP P2A-PuroR-NP (pSMARt UCOE) vector FIG. 6 shows annotated maps of the NTC9385R-UCOE-CMV-coGFP P2A-PuroR-SMAR-SV40 pA (NP-UCOE) and NTC9385R-UCOE-CMV-coGFP P2A-PuroR-SD SMAR-SA SV40 pA (NP-UCOE-SP) vectors FIG. 7 shows annotated naps of the NTC9385R-SP-UCOE-CMV-GFP SMARter (NP-SMARter-SP) and NTC9385R-SP-UCOE-CMV-GFP CMARter (NP-CMARter-SP) vectors FIG. 8 shows annotated maps of the NTC9385R-UCOE EF1-coGFP SD-SMAR SA SV40 pA (NP-UCOE-EF1-SP) and NTC9385R-UCOE EF1-coGFP-SD SMAR R6K-R-OUT-SA pA (UCOE-EF1-SP-NP) vectors FIG. 9 shows annotated maps of the NTC9385R-SP-ELE4-CMV-GFP CMARter (NP-Ele40-CMARter-SP) vector FIG. 10 shows improved expression of established S/MAR vectors with flanking SD and SA sites. Left panel: MFI of HEK293T cells established with a S/MAR vector with and without splice junctions. The vectors contain NP bacterial region, the genomic insulator UCOE, the expression cassette GFP-2A-PuroR driven by the CMV promoter and the interferon beta S/MAR in the 3' UTR with (Nano-S/MAR-splice=NP-UCOE-SP; NTC9385R-UCOE-CMV-coGFP P2A-PuroR-SD SMAR-SA SV40 pA FIG. 6) or without (NP-UCOE: NTC9385R-UCOE-CMV-coGFP P2A-PuroR-SMAR-SV40 pA, FIG. 6) S/MAR flanking SD and SA sites. Right panel: the improved transcription expression is confirmed by real time PCR analysis. The expression of the transgene GFP was normalized to the housekeeping gene GAPDH.

Figure 11:
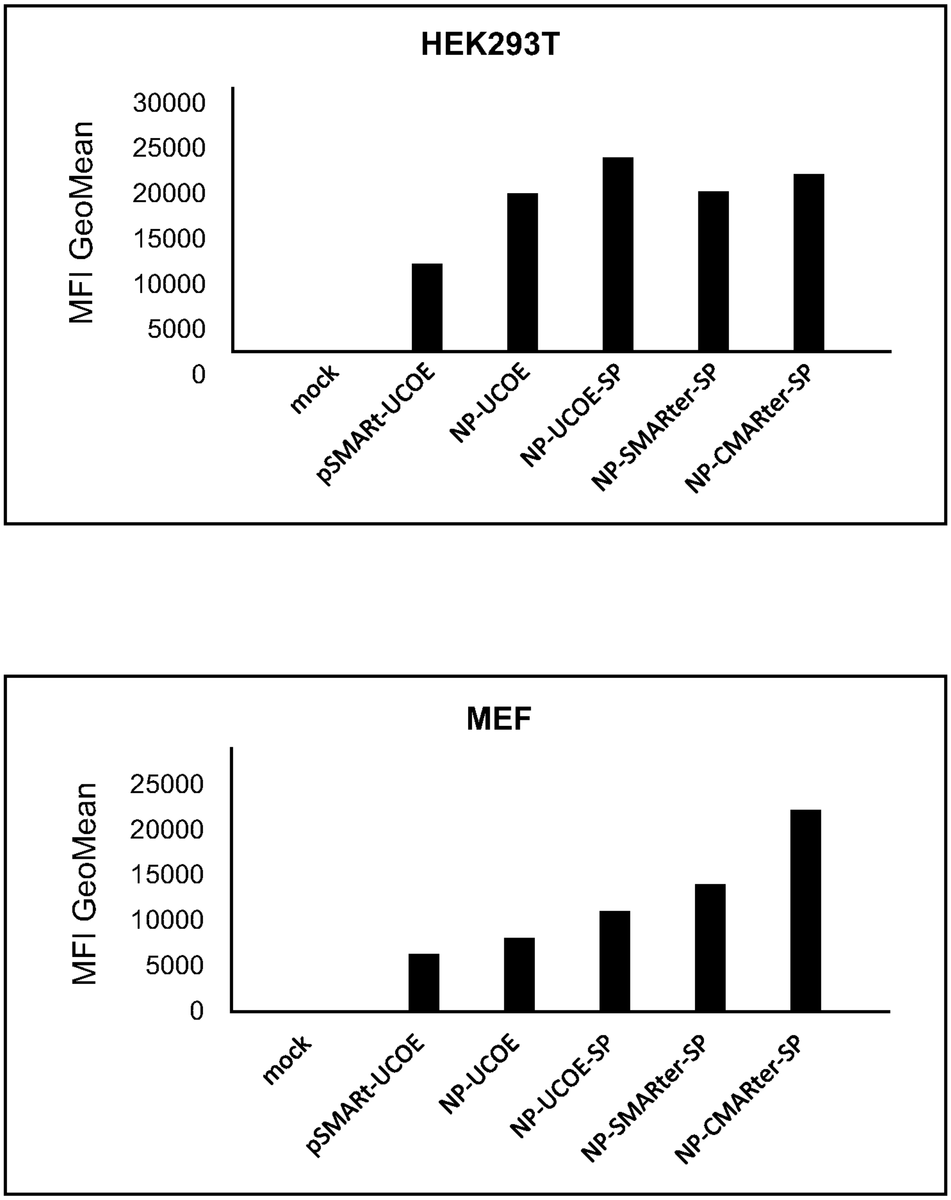
FIG. 11 depicts improved expression of established S/MAR vectors with flanking SD and SA sites. MFI of established cells (HEK293T and primary Mouse Embryonic Fibroblast) with vectors harboring different S/MARs with and without flanking SD and SA sites. Vector names are as in FIGS. 5, 6 and 7.

FIG. 11 shows improved expression of established S/MAR vectors with flanking SD and SA sites. MFI of established cells (HEK293T and primary Mouse Embryonic Fibroblast) with vectors harboring different S/MARs with and without flanking SD and SA sites. Vector names are as in FIGS. 5, 6 and 7.

Figure 12:
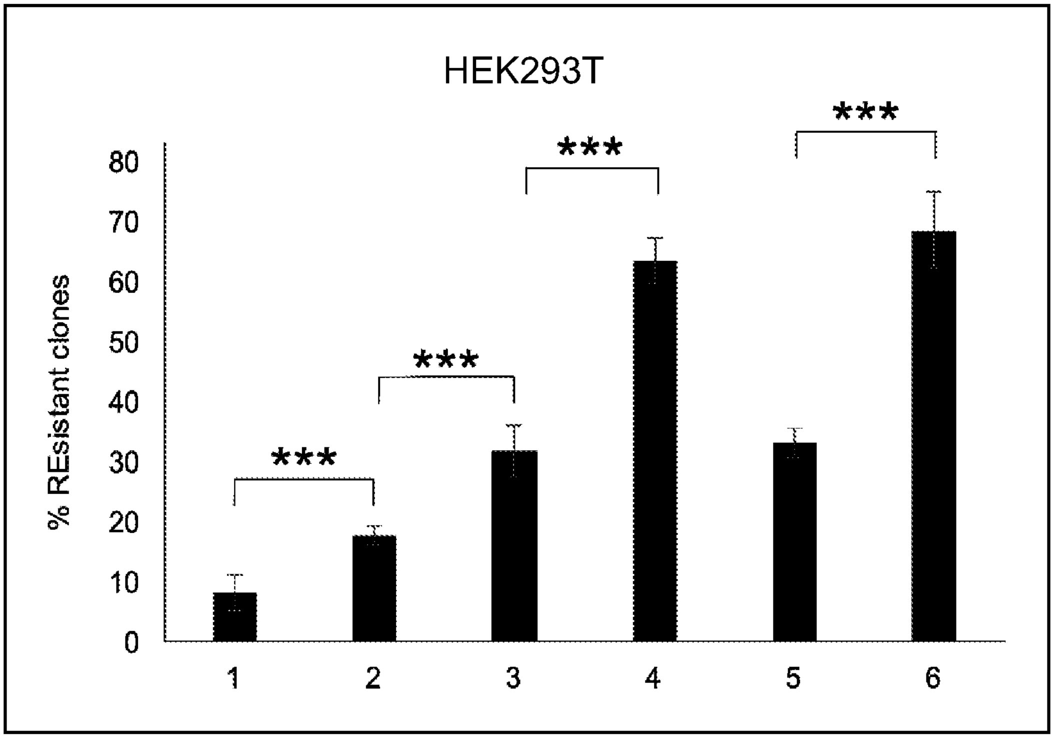
FIG. 12 depicts improved establishment of S/MAR vectors with flanking SD and SA sites. Colony forming assay conducted in HEK293T with vectors harboring two different S/MARs with and without flanking SD and SA sites. Column 1=pEPI, CMV promoter plasmid vector with a 3' UTR interferon beta S/MAR (Piechaczek, et al., 1999. *Nucleic Acids Res* 27:426); Column 2=pSMARt-UCOE (FIG. 5); Column 3=NP-UCOE (FIG. 6); Column 4=NP-UCOE-SP (FIG. 6); Column 5=pSMARt UCOE encoding the 805 bp ApoB MAR; Column 6=NP-SMARter-SP (FIG. 7).

FIG. 12 shows improved establishment of S/MAR vectors with flanking SD and SA sites. Colony forming assay conducted in HEK293T with vectors harboring two different S/MARs (interferon beta S/MAR; ApoB S/MAR, 805 bp) with and without flanking SD and SA sites. Column 1=pEPI, CMV promoter plasmid vector with a 3' UTR interferon beta S/MAR (Piechaczek, et al., Supra, 1999); Column 2=pSMARt-UCOE (FIG. 5); Column 3=NP-UCOE (FIG. 6); Column 4=NP-UCOE-SP (FIG. 6); Column 5=pSMARt UCOE encoding the 805 bp ApoB MAR; Column 6=NP-SMARter-SP (FIG. 7).

EXAMPLES

The methods of the current technology are further illustrated by the following examples. These are provided by way of illustration and are not intended in any way to limit the scope of the disclosure.

Example 1: pUC, and R6K Replication Origin Plasmid Production

RNA-OUT Antibiotic Free Selectable Marker Background:

Antibiotic-free selection is performed in *E. coli* strains containing phage lambda attachment site chromosomally integrated pCAH63-CA 7 RNA-IN-SacB (P5/6 6,6) as described in Williams, Supra, 2008. SacB (*Bacillus subtilis* levansucrase) is a counter selectable marker which is lethal to E, co cells in the presence of sucrose. Translation of SacB from the RNA-IN-SacB transcript is inhibited by plasmid encoded RNA-OUT. This facilitates plasmid selection in the presence of sucrose, by inhibition of SacB mediated lethality.

R6K Origin Vector Replication and Production Background:

The R6K gamma plasmid replication origin requires a single plasmid replication protein π that binds as a replication initiating monomer to multiple repeated 'iteron'. Use of a conditional replication origin such as R6K gamma that requires a specialized cell line for propagation adds a safety margin since the vector will not replicate if transferred to a patient's endogenous flora.

A highly minimalized R6K gamma derived replication origin (SEQ ID NO: 1) that contains core sequences required for replication was described in Williams, Supra, 2014. The NTC9385R Nanoplasmid™ backbone including this minimalized R6K origin and the RNA-OUT AF selectable marker in the spacer region, was described in Williams, Supra, 2014.

Williams, Supra, 2014 describes host strains expressing phage HK022 attachment site integrated pL promoter heat inducible π P42L, P106L and F107S high copy mutant replication (Rep) protein for selection and propagation of R6K origin Nanoplasmid™ vectors. This is an additional Nanoplasmid™ safety factor since R6K origin vectors can only replicate within the engineered Rep protein-expressing *E. coli* host strain.

S Shake Flask Production:

pUC origin plasmid production was performed in *E. coli* strain DLH5α [F-Φ80lacZΔM15 Δ(lacZYA-argF) U169 recA1 endA1 hsdR7 (rK−, mK+) phoA supE44 λ-thi-1 gyrA96 relA1] (Invitrogen, Carlsbad Calif.). R6K origin-RNA-OUT sucrose selection Nanoplasmid™ vectors was performed in host strains NTC940211 DH5α att$_2$:P$_{5/6\ 6/6}$-RNA-IN-SacB, catR; att$_{HK022}$::pL (OL1-G to T) P42L-P106I-F17S or NTC1050811 DH5α att$_{\lambda}$::P$_{5/6\ 6/6}$-RNA-IN-SacB, catR; att$_{HK022}$::pL (OL1-G to T) P42L-P106I-F107S P113S (P3−), SpecR StrepR; att$_{\varphi\lambda}$::pARA-CI857ts, tetR Shake flask production was performed using proprietary Plasmid+ shake culture medium. The seed cultures were started from glycerol stocks or colonies and streaked onto LB medium agar plates containing 50 μg/mL antibiotic (for ampR or kanR selection plasmids) or 6% sucrose (for RNA-OUT selection plasmids). The plates were grown at 30-32° C.; cells were resuspended in media and used to provide approximately 2.5 OD$_{600}$ inoculums for the 500 mL Plasmid+ shake flasks that contained 50 pg/mL antibiotic for ampR or kanR selection plasmids or 0.5% sucrose to select for RNA-OUT plasmids. Flask were grown with shaking to saturation.

Example 2: S/MAR Vector Construction

The pNTC-NP1, pNTC-NP2, pNTC-NP3, pNTC-NP4, pNTC-NP5, pNTC-NP6, pNTC-NP7, vectors encode the R6K gamma origin-RNA-OUT bacterial replication-selection region (SEQ ID NO:8) cloned into the polylinker region of a pUC57 based vector. The pNTC-3'CpG NP1 vector encode the 1 CpG R6K gamma origin-2 CpG RNA-OUT bacterial replication-selection region (SEQ ID NO:9) cloned into the polylinker region of a pUC57 based vector. Each vector has different flanking restriction sites that can be used to retrofit a target vector to R6K replication-RNA-OUT selection. The 5' and 3' polylinker sequences flanking the R6K-RNA-OUT insert in the pNTC-NP 1-7 vectors and pNTC-3×CpG NP1 are shown in Table 1.

TABLE 1 pNTC multiple cloning site flanked R6K Origin-RNA-OUT selection marker vectors

| Vector | R6K 5' flanking restriction sites | trpA term | R6K origin | Linker site | RNA OUT Selection marker | RNA-OUT 3' flanking restriction site |
|---|---|---|---|---|---|---|
| pNTC-NF1 (SEQ ID NO: 10) | EcoRI, SacI, KpnI, NruI, NsiI, XmaIII, NotI, NheI | Yes | SEQ ID NO: 1 | DraIII[a] | SEQ ID NO: 5 | NheI BamHI, XmaI, ApaI, SalI HincII, PstI, StuI, AatI, SphI, HindIII (in R6K) |
| pNTC-NP2 (SEQ ID NO: 11) | EcoRI, SacI, KpnI, NruI, NsiI, XmaIII, NotI, NheI | Yes | SEQ ID NO: 1 | DraIII[a] | SEQ ID NO: 5 | SpeI, XmaI, SspI BamHI, XmaI, ApaI, SalI, HincII, PstI, StuI, AstI, SphI, HindIII (in R6K) |
| pNTC-NP3 (SEQ ID NO: 12) | EcoRI, SacI, KpnI, NruI, NsiI, XmaIII, NotI, NheI | Yes | SEQ ID NO: 1 | DraIII[a] | SEQ ID NO: 5 | KpnI, SacI BanHI, XmaI, ApaI, SalI, HincII, PstI, StuI, AatI, SphI, HindIII (in R6K) |
| pNTC-NP4 (SEQ ID NO: 13) | NheI, XmaIII, NotI, NsiI, NruI, KpnI, SacI, BamHI, XmaI, ApaI, SalI, HincII, SfcI, PstI, StuI, AatI, SphI, HindIII (in R6K) | Yes | SEQ ID NO: 1 | DraIII[a] | SEQ ID NO: 5 | EcoRI, SacI, KpnI |
| pNTC-NP5 (SEQ ID NO: 14) | KasI, NheI | Yes | SEQ ID NO: 1 | DraIII[a] | SEQ ID NO: 5 | KpnI AflIII PstI, AatI, SphI, HindIII (in R6K) |
| pNTC-NP6 (SEQ ID NO: 15) | EcoRI, PstI, EcoRV, BstXI, NotI, NheI | Yes | SEQ ID NO: 1 | DraIII[a] | SEQ ID NO: 5 | KpnI, ApaI, PvuI, SalI, SacI |
| pNTC-NP7 (SEQ ID NO: 16) | BssHII PacI NheI | Yes | SEQ ID NO: 1 | DraIII[a] | SEQ ID NO: 5 | KpnI PacI BssHII |
| pNTf 3x CpG NpI (SEQ ID NO: 17) | XhoI, XbaI, ApaI, SalI, HincII, PstI, StuI, AatI, SphI, HindIII (in R6K) | No | SEQ ID NO: 2 | BsrGI | SEQ ID NO: 7 | EcoRI, SacI, KpnI, NruI, NsI, XmaIII, NotI, NheI, KpnI |

[a]Non-palindromic unique 3 bp NNN sticky end DraIII site (CACNNNGTG) separating R6K and RNA-OUT of sequence CACGTTGTG can be used to assemble R6K and RNA-OUT front separate pNTC vectors in directional multi-fragment ligation reactions S/MAR vector pUC origin-antibiotic selection bacterial backbone retrofits to R6K-RNA-OUT (i.e., Nanoplasmid, NP, vectors) were performed by 1) selecting restriction sites that flank the pUC origin and antibiotic selection marker region in the target S/MAR vector;
2) Identifying a pNTC-NP compatible polylinker-R6K-RNA-OUT polylinker cassette (either pNTC-NP1, 2, 3, 4, 5, 6, or 7; Table 1);
3) Excising the pUC origin antibiotic selection marker region and replacing with the selected R6K origin RNA-OUT region using the selected restriction digestion approach and standard ligase mediated cloning.

In some cases, the R6K origin and RNA-OUT units were assembled in multi-fragment ligations from separate restriction fragments using the non-palindromic DraIII linker site (see Table 1).

Example vector maps and vector characteristics of the original pUC origin-antibiotic selection marker vector (e.g. pSMARt UCOE; FIG. 5) and the retrofitted R6K origin-RNA-OUT antibiotic free selection marker vector (e.g. NP-UCOE: FIG. 6) are shown.

The SD-S/MAR-SA 3' UTRs were made as synthetic genes as follows. A splice donor site (SEQ ID NO: 25) with 5' BglII and NsiI cloning sites and a 3' XhoI cloning site (FIG. 1) was incorporated 5' to the S/MAR, while a splice acceptor site (SEQ ID NO: 26) with 5' EcoRI and 3' BamHI cloning sites (FIG. 1) was incorporated 3' to the S/MAR. The genes were synthesized at Genscript (Piscataway, NJ) and cloned in place of the S/MAR in existing SMAR-NP vectors using standard restriction fragment ligation mediated cloning. For example, the interferon beta S/MAR (SEQ ID NO: 18) (e.g. NP-UCOE vector, FIG. 6) was replaced with the splice donor-interferon beta S/MAR-splice acceptor (SEQ ID NO: 19) (e.g. NP-UCOE-SP vector. FIG. 6; NP-UCOE-EF1-SP, FIG. 8) or splice donor-interferon beta S/MAR (-AATAAA)-splice acceptor (SEQ ID NO:20) or splice donor-interferon beta M18 S/MAR-splice acceptor (SEQ ID NO:21). Splice donor-interferon beta S/MAR (-AATAAA) was designed to remove S/MAR encoded AATAAA(N) transcription termination signals with an AATATT(T) MAR motif (FIG. 2). The 805 bp ApoB S/MAR was replaced with the splice donor-805 bp ApoB S/MAR-splice acceptor version (SEQ ID NO: 22) (e.g. NP-SMARter-SP, FIG. 7) while the 525 bp ApoB S/MAR was replaced with the splice donor-525 bp ApoB S/MAR-splice acceptor version (SEQ ID NO: 23) (e.g. NP-CMARter-SP, FIG. 7; NP-Ele40-CMARter-SP, FIG. 9). Additional NP constructs with alternative transgenes, promoters, 5' UTR introns, or ELE40 or UCOE elements were made by standard restriction fragment ligation mediated cloning. All constructs were verified correct by restriction digestion and sequencing.

Example 3: S/MAR Vector Expression after Transient Transfection

Adherent HEK293 (human embryonic kidney) and A549 (human lung carcinoma), cell lines were obtained from the American Type Culture Collection (Manassas, VA, USA). Cell lines were propagated in Dulbecco's modified Eagle's medium/F12 containing 10% fetal bovine serum and split (0.25% trypsin-EDTA) using Invitrogen (Carlsbad. Calif., USA) reagents and conventional methodologies. For transfections, cells were plated on 24-well tissue culture dishes, plasmids were transfected into cell lines using Lipofectamine 2000 following the manufacturer's instructions (Invitrogen).

Total cellular lysates for EGFP determination were prepared by resuspending cells in cell lysis buffer (CellLytic M, Sigma, St Louis, MO, USA), lysing cells by incubating for 30 min at 37° C., followed by a freeze-thaw cycle at −80° C. Lysed cells were clarified by centrifugation and the supernatants assayed for EGFP by FLX800 microplate fluorescence reader (Bio-Tek, Winooski, VT, USA). The results are summarized in Tables 2-4.

TABLE 2

Transient expression of S/MAR vectors after transfection into A549 and HEK293 cell lines

| Plasmid | Promoter | Intron | 3-UTR | A549 GFP[a] | HFK GFP[a] |
|---|---|---|---|---|---|
| NTC9385R- UCOE EF1 -coGFP - SMAR SV40 pA | UCOE EF1 | None | hIFNB SMAR- SV40 pA | 552 ± 95 | 5168 ± 202 |
| NTC9385R- UCOE EF1 -coGFP SD -SMAR SA SV40 pA (NP-UCOE-EF1-SP -FIG. 8) | UCOE EF1 | None | SD hIFNB SMAR SA -SV40 pA | 1139 ± 181 | 13909 ± 1068 |
| NTC9385R- UCOE EF1-coGFP- SMAR R6K-R-OUT-pA | UCOE EF1 | None | hIFNB SMAR- R6K-R-OUT RBG pA | 607 ± 217 | 7552 ± 1754 |
| NTC9385R- UCOE EF1-coGFP- SD SMAR R6K-R-OUT-SA pA (UCOE-EF1-SP-NP -FIG. 8) | UCOE EF1 | None | SD hIFNB SMAR- R6K-R-OUT SA RBG pA | 961 ± 83 | 12956 ± 848 |
| NTC9385R- UCOE EF1 -coGFP- SD M18 SMAR R6K-R-OUT-SA pA | UCOE EF1 | None | SD M18 SMAR- R6K-R-OUT SA RBG pA | 2088 ± 449 | 16761 ± 954 |
| NTC9385R- UCOE EF1 -coGFP SD -M18 SMAR SA SV40 pA | UCOE EF1 | None | SD M18 SMAR SA -SV40 pA | 3190 ± 386 | 22640 ± 1129 |

[a]Results presented are mean fluorescent units ± standard deviation at 2 days post transfection

TABLE 3

| Transient expression of S/MAR vectors after transfection into A549 and HEK293 cell lines | | | | | |
|---|---|---|---|---|---|
| Plasmid | Promoter | Intron | 3-UTR | A549 GFP | HEK GFP |
| NTC9385R- EF1 -coGFP -SMAR SV40 pA | EF1 | None | hIFNB SMAR-SV40 pA | 1221 ± 44 | 2038 ± 131 |
| NTC9385R- UCOE EF1 -coGFP -SMAR SV40 pA | UCOE EF1 | None | hIFNB SMAR-SV40 pA | 2251 ± 122 | 7339 ± 304 |
| NTC9385R- UCOE EF1 -coGFP SD -SMAR SA SV40 pA (NP-UCOE-EF1-SP -FIG. 8) | UCOE EF1 | None | SD hIFNB SMAR SA -SV40 pA | 6205 ± 420 | 24507 ± 2501 |
| NTC9385R- UCOE EF1 -coGFP SD -SMAR(-AATAAA) SA SV40 pA | UCOE EF1 | None | SD hIFNB SMAR-AATAAA SA -SV40 pA | 4708 ± 359 | 18910 ± 1278 |
| NTC9385R- EF1-coGFP-SMAR R6K-R-OUT- pA | EF1 | None | hIFNB SMAR-R6K-R-OUT RBG pA | 1240 ± 164 | 1896 ± 189 |
| NTC9385R- UCOE EF1-coGFP-SMAR R6K-R-OUT-pA | UCOE EF1 | None | hIFNB SMAR-R6K-R-OUT RBG pA | 1540 ± 180 | 4996 ± 322 |
| NTC9385R- UCOE EF1-coGFP-SD SMAR R6K-R-OUT-SA pA (UCOE-EF1-SP-NP -FIG. 8) | UCOE EF1 | None | SD hIFNB SMAR-R6K-R-OUT SA RBG pA | 4843 ± 604 | 19247 ± 1693 |
| NTC9385R- UCOE EF1-coGFP-SD M18 SMAR R6K-R-OUT-SA pA | UCOE EF1 | None | SD M18 SMAR-R6K-R-OUT SA RBG pA | 10021 ± 753 | 27981 ± 1121 |
| NTC9385R- UCOE EF1 -coGFP SD -M18 SMAR SA SV40 pA | UCOE EF1 | None | SD M18 SMAR SA -SV40 pA | 9751 ± 821 | 29019 ± 2744 |
| NTC9385R-UCOE CMV-coGFP P2A-PuroR -SMAR-SV40 pA (NP-UCOE-FIG.6) | UCOE CMV | pCI | hIFNB SMAR-SV40 pA | 2104 ± 74 | 8478 ± 320 |
| NTC9385R-UCOE-CMV-coGFP P2A-PuroR - SD SMAR- SA SV40 pA (NP-UCOE-SP -FIG.6) | UCOE CMV | pCI | SD hIFNB SMAR SA -SV40 pA | 3526 ± 102 | 14278 ± 2664 |
| NTC9385R-UCOE-CMV-coGFP P2A-PuroR - SD SMAR(-AATAAA)- SA SV40 pA | UCOE CMV | pCI | SD hIFNB SMAR-AATAAA SA -SV40 pA | 2876 ± 376 | 13425 ± 1331 |

[a] Results presented are mean fluorescent units ± standard deviation at 2 days post transfection The results presented in Tables 2 and 3 demonstrate that with a UCOE-EF1 promoter no intron coGFP transgene transcription unit the human IFNB SMAR flanked by SD/SA improves expression in both HEK293 and A549 cell lines compared to human IFNB SMAR without SD/SA sites. Improved expression was observed in 2 SD/SA configurations (flanking SMAR, or flanking SMAR+R6K-RNA-OUT NP bacterial region). The M18 SMAR (derived from human IFNB SMAR) flanked by SD/SA has high expression like the parent human IFNB SMAR flanked by SD/SA.

In addition, the results in Table 3 show improved expression in UCOE-CMV promoter pCI intron coGFP transgene transcription unit (i.e., improved expression with two different promoters, with or without a 5' UTR encoded intron). Improved expression is also observed with different polyadenylation signals (SV40 or RBG derived) or with the bacterial region cloned in the 3' UTR along with the S/MAR (e.g. UCOE-EF1-SP-NP—FIG. 8).

TABLE 4

| Transient expression of S/MAR vectors after transfection into A549 and HEK293 cell lines | | | | | |
|---|---|---|---|---|---|
| Plasmid | Promoter | 5' UTR Intron | 3' UTR | T = 2 day A549 GFP | T = 2 day HEK GFP |
| NTC9385R- EF1-coGFP -SMAR SV40 pA | EF1 | None | hIFNB SMAR-SV40 pA | 525 ± 37 | 1377 ± 111 |
| NTC938SR- UCOE EF1 -coGFP -SMAR SV40 pA | UCOE EF1 | None | hIFNB SMAR-SV40 pA | 1848 ± 163 | 12980 ± 1005 |
| NTC9385R- UCOE EF1 -coGFP SD -SMAR SA SV40 pA (NP-UCOE-EF1-SP -FIG. 8) | UCOE EF1 | None | SD hIFNB SMAR SA -SV40 pA | 3091 ± 169 | 22354 ± 1686 |
| NTC9385R- UCOE EF1 -coGFP SD -SMAR(-AATAAA) SA SV40 pA | UCOE EF1 | None | SD hIFNB SMAR-AATAAA SA -SV40 pA | 2311 ± 413 | 14768 ± 1628 |

TABLE 4-continued

Transient expression of S/MAR vectors after transfection into A549 and HEK293 cell lines

| Plasmid | Promoter | 5' UTR Intron | 3' UTR | T = 2 day A549 GFP | T = 2 day HEK GFP |
|---|---|---|---|---|---|
| NTC9385R- UCOE EF1 -coGFP SD - M18 SMAR SA SV40 pA | UCOE EF1 | None | SD M18 SMAR SA - SV40 pA | 4833 ± 462 | 21254 ± 6296 |
| NTC9385R-SP-UCOE-EF1-GFP SMARter = coGFP | UCOE EF1 | None | SD SMARter SA - SV40 pA | 2878 ± 233 | 13688 ± 1873 |
| NTC9385R-SP-UCOE-EF1-GFP SMARter = coGFP | ELE40 EF1 | None | SD SMARter SA - SV40 pA | 990 ± 175 | 3349 ± 341 |
| pMAX-UCOE-coGFP P2A-PuroR-NP (pSMARt UCOE -FIG. 5) | UCOE CMV | pCI | hIFNB SMAR-SV40 pA | 933 ± 117 | 6193 ± 533 |
| NTC9385R-UCOE-CMV-coGFR P2A-PuroR -SMAR-SV40 pA (NP-UCOE -FIG. 6) | UCOE CMV | pCI | hIFNB SMAR-SV40 pA | 1081 ± 85 | 8216 ± 211 |
| NTC9385R-UCOE-CMV- coGFR P2A-PuroR - SD SMAR- SA SV40 pA (NP-UCOE-SP -FIG. 6) | UCOE MV | pCI | SD hIFNB SMAR SA - SV40 pA | 1857 ± 207 | 12596 ± 1531 |
| NTC9385R-UCOE-CMV- coGFP P2A-PuroR - SD SMAR(-AATAAA)- SA SV40 pA | UCOE CMV | pCI | SD hIFNB SMAR-AATAAA SA -SV40 pA | 2204 ± 70 | 13901 ± 1024 |
| NTC9385R-SP-UCOE-CMV-GFR SMARter = coGFP P2A-PuroR (NP-SMARter-SP -FIG. 7) | UCOE CMV | pCI | SD SMARter SA - SV40 pA | 917 ± 113 | 8091 ± 449 |
| NTC9385R-SP-UCOE-CMV-GFR CMARter = coGFP P2A-PuroR (NP-CMARter-SP -FIG. 7) | UCOE CMV | pCI | SD CMARter SA - SV40 pA | 3875 ± 230 | 12020 ± 624 |
| NTC9385R-SP-Ele40-CMV-GFR SMARter = coGFP P2A-PuroR | ELE40 CMV | pCI | SD SMARter SA - SV40pA | 1524 ± 59 | 5483 ± 393 |

[a] Results presented are mean fluorescent ± standard deviation at 2 days post transfection The results presented in Table 4 further demonstrates human IFNB SMAR flanked by SD/SA improves expression in both HEK293 and A549 cell lines compared to human IFNB SMAR without SD/SA site with the UCOE-EF1 promoter no intron coGFP transgene transcription unit and the UCOE-CMV promoter pCI intron coGFP transgene transcription unit (i.e., improved expression with two different promoters, with or without a 5' UTR encoded intron). Additionally. CMARter SMAR flanked by SD/SA has higher expression than human IFNB SMAR flanked by SD/SA. The improved performance using EF1 or CMV promoter expressed SD-interferon beta S/MAR-SA compared to interferon beta S/MAR (which contains transcription termination motifs and demonstrated transcription termination internal to the S/MAR; FIG. 2, Stehle et al, Supra, 2003) teaches that the mechanism for improved performance cannot be simply splicing, since the results with the unmodified S/MAR predict that there would be no transcription of the splice acceptor site due to S/MAR internal transcription termination. Consistent with this, replacement of the S/MAR internal AATAAA(N) transcription termination signals with an AATATT(T) showed no improvement over the parent transcription terminator encoding S/MAR with EF1 or CMV promoter constructs (Tables 3 and 4: SD hIFNB SMAR-AATAAA SA versus SD hIFNB SMAR SA).

If desired, the results show that replacement of S/MAR AATAAA(N) transcription termination signals with an AATAT(T) MAR motif resulted in a functional S/MAR, demonstrating that this approach can be used to remove transcription terminator signals from S/MAR elements described in the art if desired. Alternative motifs can be substituted for AATATT(T), for example, AT rich motifs enriched in S/MARs as described by Liebeich et al., Supra, 2002. While not necessary with the interferon beta S/MAR above, the AATAAA motif replacement method allows adaption of S/MARs in the art to be utilized in 3' UTRs of the invention, without reducing expression through AATAAA motif-mediated premature transcription termination should it occur with other S/MARs.

Collectively, the results demonstrate the vectors of the current invention solve the suboptimal expression level limitation of S/MAR based vectors described in the an.

Example 4: S/MAR Vector Expression after Episome Establishment

Expression from NP-UCOE (FIG. 6) and NP-UCOE-SP (FIG. 6) was determined after episomal establishment in cell line HEK293. Cells were established with the standard protocols which required the application of Puromycin (0.5 pg/ml) for one week before expansion for at least 30 days (Wong and Harbottle, 2013 *Mol Ther Nucleic Acids* 2:e115). The established populations were analysed for the expression of the reporter gone GFP via FACS and the GFP RNA levels were evaluated via qPCR. The results (FIG. 10) demonstrate that human IFNB SMAR flanked by SD/SA improves mRNA transcription and GFP transgene expression compared to human IFNB SMAR without SD/SA site after episomal establishment in the HEK293 cell line. A second experiment demonstrated GFP transgene expression of SD-S/MAR-SA vectors NP-UCOE-SP (FIG. 6), NP-SMARter-SP (FIG. 7) and NP-CMARter-SP (FIG. 7) were improved compared to non SD-SA vector NP-UCOE (FIG. 6) after episomal establishment in HEK293 cell line and primary Mouse Embryonic Fibroblast cells.

These results with established cell lines demonstrate the vectors of the current invention solve the gene silencing limitation of S/MAR based vectors described in the art.

Example 5: S/MAR Vector Expression after Episome Establishment

The efficacy in establishing cells was also tested in HEK293T through colony forming assay (Wong and Harbottle, Supra, 2013) with vectors harboring two different S/MARs (interferon beta S/MAR; ApoB S/MAR, 805 bp) with and without flanking SD and SA sites. The results demonstrated (FIG. 12) that with both the interferon beta S/MAR and the ApoB S/MAR flanking SD and SA sites dramatically improved efficacy in generating established cells (i.e., producing the highest number of colonies).

These results demonstrate the vectors of the current invention solve the low establishment rate limitation of S/MAR based vectors described in the art.

SUMMARY

While the above description contains many examples, these should not be construed as limitations on the scope of the disclosure, but rather should be viewed as an exemplification of preferred embodiments thereof. Many other variations are possible.

The vector methods and compositions disclosed herein and evaluations presented above demonstrates 3' UTR SD-SMAR-SA compositions improved expression and or episomal establishment compared to non SD-SA versions. Improved performance is not S/MAR specific since performance improvement is observed with various S/MARs. Improved performance is also not vector transcription unit specific, since performance improvement is observed with SD-SMAR-SA linked to various promoters, 5' UTRs, transgenes, and polyA signals. Improved performance is observed with or without upstream introns, and with S/MARs containing transcription termination motifs that terminate transcription internal to the S/MAR. Thus, the 3' UTR SD-SMAR-SA vectors of the disclosure are broadly applicable to improve self-replicating non-integrative episomal vertebrate expression vector performance.

The vectors of the current technology can utilize alternative splice donor sites described in the art substituted for the pCI intron derived splice donor. Likewise, an alternative splice acceptor site described in the art could be substituted for the pCI intron derived splice acceptor. For example, splice donors and acceptors may be derived from the HTLV-IR-Rabbit β globin hybrid intron, HTLV-IR CMV hybrid intron, CMV intron, CpG free intron I 140, Human β globin Murine IgG chimeric intron, Adenovirus leader-Murine IgG chimeric intron, Rabbit β globin intron, Truncated CMV intron, CAG (Chicken β Actin-rabbit β globin) intron, CMV-Rabbit β globin hybrid intron disclosed in Williams, Supra, 2014 or other introns described in the art.

The various alternative S/MARs described in the art could also be used in the vectors of the current technology. If desired, internal transcription termination motifs can be removed by motif replacement as described herein. However, this may not be necessary with many S/MARs, since S/MAR vector performance was improved by adding flanking SD and SA sites to the Interferon B S/MAR which has internal transcription termination motifs and demonstrated S/MAR internal transcription termination.

The vectors may encode a diversity of transgenes different from the examples provided herein, for example, antigen genes for a variety of pathogens, or therapeutic genes such as hypoxia inducible factor, keratinocyte growth factor, factor IX, factor VIII, Fanconi anemia complementation group A protein, homogentisate dioxygenase, etc or polyproteins such as a reprogramming factor polyprotein.

Likewise, the vectors may utilize a diversity of RNA Pol II promoters different from the CMV and elongation factor 1 (EF1) promoter examples provided herein, for example, constitutive promoters such as the chicken β-actin promoter, the β-actin promoter from other species, the phosphoglycerokinase (PGK) promoter, the spleen focus-forming virus (SFFV) promoter, the Rous sarcoma virus (RSV) promoter, the human serum albumin (SA) promoter, the thyroxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EP1α) promoters, CpG free versions of the human or murine CMV-derived enhancer elements combined with the elongation factor 1α (EF1α) promoters, the albumin promoter combined with an α-fetoprotein MERII enhancer, etc. or the diversity of tissue specific or inducible promoters know in the art such as the muscle specific promoters muscle creatine kinase (MCK), and CS-12 or the liver-specific promoters apolipoprotein A-I (ApoA1), α-1 antitrypsin (AAT) promoter, AAT-TTR promoter, SERP-TTR promoter, and ApoE-hAAT, or T-cell promoters such as hTCR8.1, CD4 and WASp Additionally, for Nanoplasmid vectors, the Nanoplasmid bacterial region can utilize various orientations of the R6K replication origin, and the RNA selectable marker. For example, any of the eight orientations of the R6K replication origin, and the RNA selectable marker in vectors of the current technology may be used (i.e., ←Pol III replication origin RSM→; ←Pol III replication origin←RSM; Pol III replication origin→RSM←Pol III replication origin→←RSM; ←RSM Pol III replication origin→; ←RSM←III replication original RSM→Pol III replication origin→; RSM→←Pol III replication origin). The bacterial region can be encoded within the spacer region or within an intron, or within the 3' UTR along with the S/MAR. The R6K origin and the RNA selectable marker may be encoded separately in the spacer region, an intron, and a 3' UTR as disclosed in Williams. Supra, 2015.

Further, a variety of RNA selectable markers know in the art may be substituted for RNA-OUT.

Thus, the reader will see that the improved self-replicating non-integrative episomal vertebrate expression vectors of the current technology provide for an approach to improve non-integrative episomal replication plasmid encoded transgene expression.

Accordingly, the scope of the disclosure should be determined not only by the embodiments illustrated, but also by the appended claims

What is claimed is:

1. A method for improving the expression and establishment efficiency of a self-replicating non-integrative episomal S/MAR expression vector in a target vertebrate cell comprising the following steps:

a. providing an episomal S/MAR expression vector comprising:

i. a bacterial replication-selection region comprising a bacterial origin of replication and a selectable marker gene;

ii. a transcription unit for expression of a transgene in a vertebrate cell, comprising a promoter, a 5' UTR, a transgene, and a 3' UTR;

iii. an S/MAR insert located within said 3' UTR; and b. modifying the episomal S/MAR expression vector such that the S/MAR is flanked by a 5' splice donor site and a 3' splice acceptor site within said 3' UTR, whereby the resultant self-replicating non-integrative episomal S/MAR expression vector has improved expression and establishment efficiency after transfection of a vertebrate cell.

2. The method of claim 1, wherein said S/MAR insert contains internal AATAAA transcription termination motifs.

3. The method of claim 2 further comprising replacing said AATAAA transcription termination motifs in said S/MAR with AATATT motifs.

4. The method of claim 1, wherein said S/MAR is selected from the group consisting of human Interferon beta S/MAR, M18 S/MAR, and Apolipoprotein B S/MAR.

5. The method of claim 1, wherein said SMAR flanked by a 5' splice donor site and a 3' splice acceptor site has at least 95% sequence identity to a sequence selected from the group consisting of SEQ ID NO: 19, SEQ ID NO: 20, SEQ ID NO: 21, SEQ ID NO: 22, and SEQ ID NO: 23.

6. The method of claim 1, wherein said bacterial origin of replication is an R6K gamma replication origin.

7. The method of claim 1, wherein said bacterial origin of replication is an R6K gamma replication origin with at least 95% sequence identity to a sequence selected from the group consisting of SEQ ID NO: 1, SEQ ID NO: 2, SEQ ID NO: 3, and SEQ ID NO: 4.

8. The method of claim 1, wherein said selectable marker gene is a functional variant of an RNA-OUT selectable marker gene, said functional variant having at least 95% sequence identity to a sequence selected from the group consisting of SEQ ID NO: 5 and SEQ ID NO: 7, and wherein a gene product of said RNA-OUT selectable marker gene regulates an RNA-IN regulated selectable marker gene.

9. The method of claim 1, wherein a gene product of said selectable marker gene is an RNA-OUT RNA with at least 95% sequence identity to SEQ ID NO: 6.

10. The method of claim 1, wherein said bacterial replication-selection region comprising a bacterial origin of replication and a selectable marker is a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

11. The method of claim 1, where said 5' UTR further encodes an intron.

12. The method of claim 1, where said transcription unit further encodes an expression enhancer positioned upstream of the promoter.

13. The method of claim 12, wherein said expression enhancer has at least 95% sequence identity to a sequence selected from the group consisting of SEQ ID NO: 27, and SEQ ID NO: 28.

14. The method of claim 1, wherein said splice donor site has at least 95% sequence identity to SEQ ID NO:25.

15. The method of claim 1, wherein said splice acceptor site has at least 95% sequence identity to SEQ ID NO: 26.

16. The method of claim 1, wherein said self-replicating non-integrative episomal S/MAR expression vector is selected from the group consisting of plasmid vector, Nanoplasmid vector, Mini-Intronic Plasmid, Integration-Deficient Lentivirus vector, and Non-integrating Lentiviral vectors.

17. A covalently closed circular recombinant DNA molecule comprising:

a. a transcription unit for expression of a transgene in a vertebrate cell, comprising a promoter, a 5' UTR, a transgene, and a 3' UTR;

b. an S/MAR located within said 3' UTR, wherein said S/MAR is flanked by a 5' splice donor site and a 3' splice acceptor site;

c. an R6K gamma replication origin with at least 95% sequence identity to a sequence selected from the group consisting of SEQ ID NO: 1, SEQ ID NO: 2, SEQ ID NO: 3, and SEQ ID NO: 4; and d. a functional variant of an RNA-OUT selectable marker gene comprising at least a 95% sequence identity to a sequence selected from the group consisting of SEQ ID NO: 5 and SEQ ID NO: 7, and wherein a gene product of said functional variant of the RNA-OUT selectable marker gene regulates an RNA-IN regulated selectable marker gene.

18. The recombinant DNA molecule of claim 17, wherein said R6K gamma replication origin and said RNA-OUT RNA selectable marker comprise a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

19. The recombinant DNA molecule of claim 17, wherein said S/MAR contains internal AATAAA transcription termination motifs.

20. The recombinant DNA molecule of claim 17, wherein said S/MAR contains internal AATATT transcription termination motifs.

21. The recombinant DNA molecule of claim 17, wherein said S/MAR is selected from the group consisting of human Interferon beta S/MAR, M18 S/MAR, and Apolipoprotein B S/MAR.

22. The recombinant DNA molecule of claim 17, wherein said S/MAR flanked by a 5' splice donor site and a 3' splice acceptor site has at least 95% sequence identity to a sequence selected from the group consisting of SEQ ID NO: 19, SEQ ID NO: 20, SEQ ID NO: 21, SEQ ID NO: 22, and SEQ ID NO: 23.

23. The recombinant DNA molecule of claim 17, where said 5' UTR further encodes an intron.

24. The recombinant DNA molecule of claim 17, where said transcription unit further encodes an expression enhancer positioned upstream of the promoter.

25. The recombinant DNA molecule of claim 17, wherein said expression enhancer has at least 95% sequence identity to a sequence selected from the group consisting of SEQ ID NO: 27, and SEQ ID NO: 28.

26. The recombinant DNA molecule of claim 17, wherein said splice donor site has at least 95% sequence identity to SEQ ID NO:25.

27. The recombinant DNA molecule of claim 17, wherein said splice acceptor site has at least 95% sequence identity to SEQ ID NO: 26.

* * * * *

SEQUENCE LISTING

```
<160> NUMBER OF SEQ ID NOS: 29

<210> SEQ ID NO 1
<211> LENGTH: 281
<212> TYPE: DNA
<213> ORGANISM: Artificial Sequence
```

<220> FEATURE:
<223> OTHER INFORMATION: R6K gamma origin

<400> SEQUENCE: 1
ggcttgttgt ccacaaccgt taaaccttaa aagctttaaa agccttatat attctttttt 60
ttcttataaa acttaaaacc ttagaggcta tttaagttgc tgatttatat taattttatt 120
gttcaaacat gagagcttag tacgtgaaac atgagagctt agtacgttag ccatgagagc 180
ttagtacgtt agccatgagg gtttagttcg ttaaacatga gagcttagta cgttaaacat 240
gagagcttag tacgtactat caacaggttg aactgctgat c 281

<210> SEQ ID NO 2
<211> LENGTH: 281
<212> TYPE: DNA
<213> ORGANISM: Artificial Sequence
<220> FEATURE:
<223> OTHER INFORMATION: 1 CpG R6K gamma origin

<400> SEQUENCE: 2
ggcttgttgt ccacaaccat taaaccttaa aagctttaaa agccttatat attctttttt 60
ttcttataaa acttaaaacc ttagaggcta tttaagttgc tgatttatat taattttatt 120
gttcaaacat gagagcttag tacgtgaaac atgagagctt agtacattag ccatgagagc 180
ttagtacatt agccatgagg gtttagttca ttaaacatga gagcttagta cattaaacat 240
gagagcttag tacatactat caacaggttg aactgctgat c 281

<210> SEQ ID NO 3
<211> LENGTH: 260
<212> TYPE: DNA
<213> ORGANISM: Artificial Sequence
<220> FEATURE:
<223> OTHER INFORMATION: CpG free R6K gamma origin

<400> SEQUENCE: 3
aaaccttaaa acctttaaaa gccttatata ttcttttttt tcttataaaa cttaaaacct 60
tagaggctat ttaagttgct gatttatatt aattttattg ttcaaacatg agagcttagt 120
acatgaaaca tgagagctta gtacattagc catgagagct tagtacatta gccatgaggg 180
tttagttcat taaacatgag agcttagtac attaaacatg agagcttagt acatactatc 240
aacaggttga actgctgatc 260

<210> SEQ ID NO 4
<211> LENGTH: 389
<212> TYPE: DNA
<213> ORGANISM: Artificial Sequence
<220> FEATURE:
<223> OTHER INFORMATION: Extended R6K gamma origin

<400> SEQUENCE: 4
tgtcagccgt taagtgttcc tgtgtcactg aaaattgctt tgagaggctc taagggcttc 60
tcagtgcgtt acatccctgg cttgttgtcc acaaccgtta aaccttaaaa gctttaaaag 120
ccttatatat tctttttttt cttataaaac ttaaaacctt agaggctatt taagttgctg 180
atttatatta attttattgt tcaaacatga gagcttagta cgtgaaacat gagagcttag 240
tacgttagcc atgagagctt agtacgttag ccatgagggt ttagttcgtt aaacatgaga 300
gcttagtacg ttaaacatga gagcttagta cgtgaaacat gagagcttag tacgtactat 360
caacaggttg aactgctgat cttcagatc 389

<210> SEQ ID NO 5
<211> LENGTH: 139
<212> TYPE: DNA
<213> ORGANISM: Artificial Sequence
<220> FEATURE:
<223> OTHER INFORMATION: RNA-OUT selectable marker

<400> SEQUENCE: 5
gtagaattgg taaagagagt cgtgtaaaat atcgagttcg cacatcttgt tgtctgatta 60
ttgatttttg gcgaaaccat ttgatcatat gacaagatgt gtatctacct taacttaatg 120
attttgataa aaatcatta 139

<210> SEQ ID NO 6
<211> LENGTH: 69
<212> TYPE: DNA
<213> ORGANISM: Artificial Sequence
<220> FEATURE:
<223> OTHER INFORMATION: RNA-OUT antisense repressor RNA

<400> SEQUENCE: 6
tcgcacatct tgttgtctga ttattgattt ttggcgaaac catttgatca tatgacaaga 60
tgtgtatct 69

<210> SEQ ID NO 7
<211> LENGTH: 139
<212> TYPE: DNA
<213> ORGANISM: Artificial Sequence
<220> FEATURE:
<223> OTHER INFORMATION: 2 CpG RNA-OUT selectable marker

<400> SEQUENCE: 7
gtagaattgg taaagagagt tgtgtaaaat attgagttcg cacatcttgt tgtctgatta 60
ttgatttttg gcgaaaccat ttgatcatat gacaagatgt gtatctacct taacttaatg 120
attttgataa aaatcatta 139

<210> SEQ ID NO 8
<211> LENGTH: 466
<212> TYPE: DNA
<213> ORGANISM: Artificial Sequence
<220> FEATURE:
<223> OTHER INFORMATION: R6K gamma origin -RNA-OUT bacterial
replication-selection region flanked by NheI and KpnI restriction
sites

<400> SEQUENCE: 8
gctagcccgc ctaatgagcg ggcttttttt tggcttgttg tccacaaccg ttaaacctta 60
aaagctttaa aagccttata tattcttttt tttcttataa aacttaaaac cttagaggct 120
atttaagttg ctgatttata ttaattttat tgttcaaaca tgagagctta gtacgtgaaa 180
catgagagct tagtacgtta gccatgagag cttagtacgt tagccatgag ggtttagttc 240
gttaaacatg agagcttagt acgttaaaca tgagagctta gtacgtacta tcaacaggtt 300
gaactgctga tccacgttgt ggtagaattg gtaaagagag tcgtgtaaaa tatcgagttc 360
gcacatcttg ttgtctgatt attgattttt ggcgaaacca tttgatcata tgacaagatg 420
tgtatctacc ttaacttaat gattttgata aaaatcatta ggtacc 466

<210> SEQ ID NO 9
<211> LENGTH: 439
<212> TYPE: DNA
<213> ORGANISM: Artificial Sequence

```
<220> FEATURE:
<223> OTHER INFORMATION: 1 CpG R6K gamma origin - 2 CpG RNA-OUT
      bacterial replication-selection region flanked by NheI and KpnI
      restriction sites

<400> SEQUENCE: 9

gctagctggc ttgttgtcca caaccattaa accttaaaag ctttaaaagc cttatatatt     60

cttttttttc ttataaaact taaaacctta gaggctattt aagttgctga tttatattaa    120

ttttattgtt caaacatgag agcttagtac gtgaaacatg agagcttagt acattagcca    180

tgagagctta gtacattagc catgagggtt tagttcatta aacatgagag cttagtacat    240

taaacatgag agcttagtac atactatcaa caggttgaac tgctgatctg tacagtagaa    300

ttggtaaaga gagttgtgta aaatattgag ttcgcacatc ttgttgtctg attattgatt    360

tttggcgaaa ccatttgatc atatgacaag atgtgtatct accttaactt aatgattttg    420

ataaaaatca ttaggtacc                                                 439


<210> SEQ ID NO 10
<211> LENGTH: 565
<212> TYPE: DNA
<213> ORGANISM: Artificial Sequence
<220> FEATURE:
<223> OTHER INFORMATION: pNTC-NP1 polylinker trpA R6K-RNA-OUT polylinker
      cloning cassette: EcoRI-HindIII

<400> SEQUENCE: 10

gaattcgagc tcggtacctc gcgaatgcat ctaggggacg gccgctagcc cgcctaatga     60

gcgggctttt ttttggcttg ttgtccacaa ccgttaaacc ttaaaagctt taaaagcctt    120

atatattctt ttttttctta taaaacttaa aaccttagag gctatttaag ttgctgattt    180

atattaattt tattgttcaa acatgagagc ttagtacgtg aaacatgaga gcttagtacg    240

ttagccatga gagcttagta cgttagccat gagggtttag ttcgttaaac atgagagctt    300

agtacgttaa acatgagagc ttagtacgta ctatcaacag gttgaactgc tgatccacgt    360

tgtggtagaa ttggtaaaga gagtcgtgta aaatatcgag ttcgcacatc ttgttgtctg    420

attattgatt tttggcgaaa ccatttgatc atatgacaag atgtgtatct accttaactt    480

aatgattttg ataaaaatca ttaggagcta gcattgggtc atcggatccc gggcccgtcg    540

actgcagagg cctgcatgca agctt                                          565


<210> SEQ ID NO 11
<211> LENGTH: 584
<212> TYPE: DNA
<213> ORGANISM: Artificial Sequence
<220> FEATURE:
<223> OTHER INFORMATION: pNTC-NP2 polylinker trpA R6K-RNA-OUT polylinker
      cloning cassette: EcoRI-HindIII

<400> SEQUENCE: 11

gaattcgagc tcggtacctc gcgaatgcat ctaggggacg gccgctagcc cgcctaatga     60

gcgggctttt ttttggcttg ttgtccacaa ccgttaaacc ttaaaagctt taaaagcctt    120

atatattctt ttttttctta taaaacttaa aaccttagag gctatttaag ttgctgattt    180

atattaattt tattgttcaa acatgagagc ttagtacgtg aaacatgaga gcttagtacg    240

ttagccatga gagcttagta cgttagccat gagggtttag ttcgttaaac atgagagctt    300

agtacgttaa acatgagagc ttagtacgta ctatcaacag gttgaactgc tgatccacgt    360

tgtggtagaa ttggtaaaga gagtcgtgta aaatatcgag ttcgcacatc ttgttgtctg    420
```

attattgatt tttggcgaaa ccatttgatc atatgacaag atgtgtatct accttaactt 480
aatgattttg ataaaaatca ttaggactag tcccgggcgc tagttattaa tattgggtca 540
tcggatcccg ggcccgtcga ctgcagaggc ctgcatgcaa gctt 584

<210> SEQ ID NO 12
<211> LENGTH: 557
<212> TYPE: DNA
<213> ORGANISM: Artificial Sequence
<220> FEATURE:
<223> OTHER INFORMATION: pNTC-NP3 polylinker trpA R6K-RNA-OUT polylinker
cloning cassette: EcoRI-HindIII

<400> SEQUENCE: 12
gaattcgagc tcggtacctc gcgaatgcat ctaggggacg gccgctagcc cgcctaatga 60
gcgggctttt ttttggcttg ttgtccacaa ccgttaaacc ttaaaagctt taaaagcctt 120
atatattctt ttttttctta taaaacttaa aaccttagag gctatttaag ttgctgattt 180
atattaattt tattgttcaa acatgagagc ttagtacgtg aaacatgaga gcttagtacg 240
ttagccatga gagcttagta cgttagccat gagggtttag ttcgttaaac atgagagctt 300
agtacgttaa acatgagagc ttagtacgta ctatcaacag gttgaactgc tgatccacgt 360
tgtggtagaa ttggtaaaga gagtcgtgta aaatatcgag ttcgcacatc ttgttgtctg 420
attattgatt tttggcgaaa ccatttgatc atatgacaag atgtgtatct accttaactt 480
aatgattttg ataaaaatca ttaggtaccg agctcggatc ccgggcccgt cgactgcaga 540
ggcctgcatg caagctt 557

<210> SEQ ID NO 13
<211> LENGTH: 557
<212> TYPE: DNA
<213> ORGANISM: Artificial Sequence
<220> FEATURE:
<223> OTHER INFORMATION: pNTC-NP4 polylinker trpA R6K-RNA-OUT polylinker
cloning cassette: HindIII-EcoRI

<400> SEQUENCE: 13
aagcttgcat gcaggcctct gcagtcgacg ggcccgggat ccgagctcgg tacctcgcga 60
atgcatctag gggacggccg ctagcccgcc taatgagcgg gctttttttt ggcttgttgt 120
ccacaaccgt taaaccttaa aagctttaaa agccttatat attctttttt ttcttataaa 180
acttaaaacc ttagaggcta tttaagttgc tgatttatat taattttatt gttcaaacat 240
gagagcttag tacgtgaaac atgagagctt agtacgttag ccatgagagc ttagtacgtt 300
agccatgagg gtttagttcg ttaaacatga gagcttagta cgttaaacat gagagcttag 360
tacgtactat caacaggttg aactgctgat ccacgttgtg gtagaattgg taaagagagt 420
cgtgtaaaat atcgagttcg cacatcttgt tgtctgatta ttgatttttg gcgaaaccat 480
ttgatcatat gacaagatgt gtatctacct taacttaatg attttgataa aaatcattag 540
gtaccgagct cgaattc 557

<210> SEQ ID NO 14
<211> LENGTH: 503
<212> TYPE: DNA
<213> ORGANISM: Artificial Sequence
<220> FEATURE:
<223> OTHER INFORMATION: pNTC-NP5 polylinker trpA R6K-RNA-OUT polylinker
cloning cassette: KasI-HindIII

<400> SEQUENCE: 14

-continued

```
ggcgccgcta gcccgcctaa tgagcgggct ttttttggc ttgttgtcca caaccgttaa     60

accttaaaag ctttaaaagc cttatatatt cttttttttc ttataaaact taaaacctta    120

gaggctattt aagttgctga tttatattaa ttttattgtt caaacatgag agcttagtac    180

gtgaaacatg agagcttagt acgttagcca tgagagctta gtacgttagc catgagggtt    240

tagttcgtta aacatgagag cttagtacgt taaacatgag agcttagtac gtactatcaa    300

caggttgaac tgctgatcca cgttgtggta gaattggtaa agagagtcgt gtaaaatatc    360

gagttcgcac atcttgttgt ctgattattg atttttggcg aaaccatttg atcatatgac    420

aagatgtgta tctaccttaa cttaatgatt ttgataaaaa tcattaggta ccacatgtcc    480

tgcagaggcc tgcatgcaag ctt                                            503
```

```
<210> SEQ ID NO 15
<211> LENGTH: 539
<212> TYPE: DNA
<213> ORGANISM: Artificial Sequence
<220> FEATURE:
<223> OTHER INFORMATION: pNTC-NP6 polylinker trpA R6K-RNA-OUT polylinker
      cloning cassette: EcoRI-SacI

<400> SEQUENCE: 15

gaattctgca gatatccatc acactggcgg ccgctagccc gcctaatgag cgggcttttt     60

tttggcttgt tgtccacaac cgttaaacct taaaagcttt aaaagcctta tatattcttt    120

tttttcttat aaaacttaaa accttagagg ctatttaagt tgctgattta tattaattt    180

attgttcaaa catgagagct tagtacgtga aacatgagag cttagtacgt tagccatgag    240

agcttagtac gttagccatg agggtttagt tcgttaaaca tgagagctta gtacgttaaa    300

catgagagct tagtacgtac tatcaacagg ttgaactgct gatccacgtt gtggtagaat    360

tggtaaagag agtcgtgtaa aatatcgagt tcgcacatct tgttgtctga ttattgattt    420

ttggcgaaac catttgatca tatgacaaga tgtgtatcta ccttaactta atgattttga    480

taaaaatcat taggtaccgg gcccccctc gatcgaggtc gacggtatcg ggggagctc     539
```

```
<210> SEQ ID NO 16
<211> LENGTH: 500
<212> TYPE: DNA
<213> ORGANISM: Artificial Sequence
<220> FEATURE:
<223> OTHER INFORMATION: pNTC-NP7 polylinker trpA R6K-RNA-OUT polylinker
      cloning cassette: BssHII-BssHII

<400> SEQUENCE: 16

gcgcgcagcc ttaattaagc tagcccgcct aatgagcggg cttttttttg gcttgttgtc     60

cacaaccgtt aaaccttaaa agctttaaaa gccttatata ttcttttttt tcttataaaa    120

cttaaaacct tagaggctat ttaagttgct gatttatatt aattttattg ttcaaacatg    180

agagcttagt acgtgaaaca tgagagctta gtacgttagc catgagagct tagtacgtta    240

gccatgaggg tttagttcgt taaacatgag agcttagtac gttaaacatg agagcttagt    300

acgtactatc aacaggttga actgctgatc cacgttgtgg tagaattggt aaagagagtc    360

gtgtaaaata tcgagttcgc acatcttgtt gtctgattat tgatttttgg cgaaaccatt    420

tgatcatatg acaagatgtg tatctacctt aacttaatga ttttgataaa aatcattagg    480

taccttaatt aactgcgcgc                                                500
```

```
<210> SEQ ID NO 17
<211> LENGTH: 530
```

<212> TYPE: DNA
<213> ORGANISM: Artificial Sequence
<220> FEATURE:
<223> OTHER INFORMATION: pNTC-3xCpG NP1 polylinker R6K-RNA-OUT polylinker cloning cassette: HindIII-EcoRI

<400> SEQUENCE: 17
aagcttgcat gcaggcctct gcagtcgacg ggccctctag actcgagctg gcttgttgtc 60
cacaaccatt aaaccttaaa agctttaaaa gccttatata ttcttttttt tcttataaaa 120
cttaaaacct tagaggctat ttaagttgct gatttatatt aattttattg ttcaaacatg 180
agagcttagt acgtgaaaca tgagagctta gtacattagc catgagagct tagtacatta 240
gccatgaggg tttagttcat taaacatgag agcttagtac attaaacatg agagcttagt 300
acatactatc aacaggttga actgctgatc tgtacagtag aattggtaaa gagagttgtg 360
taaaatattg agttcgcaca tcttgttgtc tgattattga tttttggcga aaccatttga 420
tcatatgaca agatgtgtat ctaccttaac ttaatgattt tgataaaaat cattaggtac 480
cgctagcggc cgtcccctag atgcattcgc gaggtaccga gctcgaattc 530

<210> SEQ ID NO 18
<211> LENGTH: 1973
<212> TYPE: DNA
<213> ORGANISM: Artificial Sequence
<220> FEATURE:
<223> OTHER INFORMATION: human Interferon beta S/MAR flanked by 5' BglII-XhoI site and 3' EcoRI restriction enzyme sites

<400> SEQUENCE: 18
agatctcgag ctcgatgata atgaatgtct aagttaatgc agaaacggag agacatacta 60
tattcatgaa ctaaaagact taatattgtg aaggtatact ttctttccac ataaatttgt 120
agtcaatatg ttcaccccaa aaaagctgtt tgttaacttg ccaacctcat tctaaaatgt 180
atatagaagc ccaaaagaca ataacaaaaa tattcttgta gaacaaaatg ggaaagaatg 240
ttccactaaa tatcaagatt tagagcaaag catgagatgt gtggggatag acagtgaggc 300
tgataaaata gagtagagct cagaaacaga cccattgata tatgtaagtg acctatgaaa 360
aaaatatggc attttacaat gggaaaatga tgatcttttt ctttttttaga aaaacaggga 420 aatatattta tatgtaaaaa ataaaaggga acccatatgt cataccatac acacaaaaaa 480
attccagtga attataagtc taaatggaga aggcaaaact ttaaatcttt tagaaaataa 540
tatagaagca tgccatcatg acttcagtgt agagaaaaat ttcttatgac tcaaagtcct 600
aaccacaaag aaaagattgt taattagatt gcatgaatat taagacttat ttttaaaatt 660
aaaaaaccat taagaaaagt caggccatag aatgacagaa aatatttgca acaccccagt 720
aaagagaatt gtaatatgca gattataaaa agaagtctta caaatcagta aaaaataaaa 780
ctagacaaaa atttgaacag atgaaagaga aactctaaat aatcattaca catgagaaac 840
tcaatctcag aaatcagaga actatcattg catatacact aaattagaga aatattaaaa 900
ggctaagtaa catctgtggc aatattgatg gtatataacc ttgatatgat gtgatgagaa 960
cagtacttta ccccatgggc ttcctcccca aacccttacc ccagtataaa tcatgacaaa 1020
tatactttaa aaaccattac cctatatcta accagtactc ctcaaaactg tcaaggtcat 1080
caaaaataag aaaagtctga ggaactgtca aaactaagag gaacccaagg agacatgaga 1140
attatatgta atgtggcatt ctgaatgaga tcccagaaca gaaaaagaac agtagctaaa 1200
aaactaatga aatataaata aagtttgaac tttagttttt tttaaaaaag agtagcatta 1260

-continued

```
acacggcaaa gccattttca tatttttctt gaacattaag tacaagtcta taattaaaaa   1320

tttttaaat gtagtctgga acattgccag aaacagaagt acagcagcta tctgtgctgt   1380

cgcctaacta tccatagctg attggtctaa aatgagatac atcaacgctc ctccatgttt   1440

tttgttttct ttttaaatga aaaactttat tttttaagag gagtttcagg ttcatagcaa   1500

aattgagagg aaggtacatt caagctgagg aagttttcct ctattcctag tttactgaga   1560

gattgcatca tgaatgggtg ttaaattttg tcaaatgctt tttctgtgtc tatcaatatg   1620

accatgtgat tttcttcttt aacctgttga tgggacaaat tacgttaatt gattttcaaa   1680

cgttgaacca cccttacata tctggaataa attctacttg gttgtggtgt atattttttg   1740

atacattctt ggattctttt tgctaatatt ttgttgaaaa tgtttgtatc tttgttcatg   1800

agagatattg gtctgttgtt ttcttttctt gtaatgtcat tttctagttc cggtattaag   1860

gtaatgctgg cctagttgaa tgatttagga agtattccct ctgcttctgt cttctgaaag   1920

agattgtaga aagttgatac aatttttttt tctttaaata tttgatagaa ttc          1973
```

<210> SEQ ID NO 19
<211> LENGTH: 2085
<212> TYPE: DNA
<213> ORGANISM: Artificial Sequence
<220> FEATURE:
<223> OTHER INFORMATION: Splice donor-human Interferon beta S/MAR-splice acceptor flanked by 5' BglII site and 3' BamHI restriction enzyme sites

<400> SEQUENCE: 19

```
agatctatgc atgcagaagt tggtcgtgag gcactgggca ggtaagtatc aaggttacaa     60

gacaggtctc gagctcgatg ataatgaatg tctaagttaa tgcagaaacg gagagacata    120

ctatattcat gaactaaaag acttaatatt gtgaaggtat actttctttc cacataaatt    180

tgtagtcaat atgttcaccc caaaaaagct gtttgttaac ttgccaacct cattctaaaa    240

tgtatataga agcccaaaag acaataacaa aaatattctt gtagaacaaa atgggaaaga    300

atgttccact aaatatcaag atttagagca aagcatgaga tgtgtgggga tagacagtga    360

ggctgataaa atagagtaga gctcagaaac agacccattg atatatgtaa gtgacctatg    420

aaaaaaatat ggcattttac aatgggaaaa tgatgatctt tttctttttt agaaaaacag    480

ggaaatatat ttatatgtaa aaaataaaag ggaacccata tgtcatacca tacacacaaa    540

aaaattccag tgaattataa gtctaaatgg agaaggcaaa actttaaatc ttttagaaaa    600

taatatagaa gcatgccatc atgacttcag tgtagagaaa aatttcttat gactcaaagt    660

cctaaccaca aagaaaagat tgttaattag attgcatgaa tattaagact tatttttaaa    720

attaaaaaac cattaagaaa agtcaggcca tagaatgaca gaaaatattt gcaacacccc    780

agtaaagaga attgtaatat gcagattata aaaagaagtc ttacaaatca gtaaaaaata    840

aaactagaca aaaatttgaa cagatgaaag agaaactcta aataatcatt acacatgaga    900

aactcaatct cagaaatcag agaactatca ttgcatatac actaaattag agaaatatta    960

aaaggctaag taacatctgt ggcaatattg atggtatata accttgatat gatgtgatga   1020

gaacagtact ttaccccatg ggcttcctcc ccaaaccctt accccagtat aaatcatgac   1080

aaatatactt taaaaaccat taccctatat ctaaccagta ctcctcaaaa ctgtcaaggt   1140

catcaaaaat aagaaaagtc tgaggaactg tcaaaactaa gaggaaccca aggagacatg   1200

agaattatat gtaatgtggc attctgaatg agatcccaga acagaaaaag aacagtagct   1260

aaaaaactaa tgaaatataa ataaagtttg aactttagtt ttttttaaaa aagagtagca   1320
```

ttaacacggc aaagccattt tcatattttt cttgaacatt aagtacaagt ctataattaa 1380
aaatttttta aatgtagtct ggaacattgc cagaaacaga agtacagcag ctatctgtgc 1440
tgtcgcctaa ctatccatag ctgattggtc taaaatgaga tacatcaacg ctcctccatg 1500
tttttgtttt tctttttaaa tgaaaaactt tattttttaa gaggagtttc aggttcatag 1560
caaaattgag aggaaggtac attcaagctg aggaagtttt cctctattcc tagtttactg 1620
agagattgca tcatgaatgg gtgttaaatt ttgtcaaatg ctttttctgt gtctatcaat 1680
atgaccatgt gattttcttc tttaacctgt tgatgggaca aattacgtta attgattttc 1740
aaacgttgaa ccacccttac atatctggaa taaattctac ttggttgtgg tgtatatttt 1800
ttgatacatt cttggattct ttttgctaat attttgttga aaatgtttgt atctttgttc 1860
atgagagata ttggtctgtt gttttctttt cttgtaatgt cattttctag ttccggtatt 1920
aaggtaatgc tggcctagtt gaatgattta ggaagtattc cctctgcttc tgtcttctga 1980
aagagattgt agaaagttga tacaattttt ttttctttaa atatttgata gaattcttac 2040
tgacatccac tttgcctttc tctccacagg tgtccactcg gatcc 2085

<210> SEQ ID NO 20
<211> LENGTH: 2085
<212> TYPE: DNA
<213> ORGANISM: Artificial Sequence
<220> FEATURE:
<223> OTHER INFORMATION: Splice donor-human Interferon beta S/MAR (-AATAAA)-splice acceptor flanked by 5' BglII site and 3' BamHI restriction enzyme sites

<400> SEQUENCE: 20
agatctatgc atgcagaagt tggtcgtgag gcactgggca ggtaagtatc aaggttacaa 60
gacaggtctc gagctcgatg ataatgaatg tctaagttaa tgcagaaacg gagagacata 120
ctatattcat gaactaaaag acttaatatt gtgaaggtat actttctttc cacataaatt 180
tgtagtcaat atgttcaccc caaaaaagct gtttgttaac ttgccaacct cattctaaaa 240
tgtatataga agcccaaaag acaataacaa aaatattctt gtagaacaaa atgggaaaga 300
atgttccact aaatatcaag atttagagca aagcatgaga tgtgtgggga tagacagtga 360
ggctgataaa atagagtaga gctcagaaac agacccattg atatatgtaa gtgacctatg 420
aaaaaaatat ggcattttac aatgggaaaa tgatgatctt tttctttttt agaaaaacag 480
ggaaatatat ttatatgtaa aaaatatttg ggaacccata tgtcatacca tacacacaaa 540
aaaattccag tgaattataa gtctaaatgg agaaggcaaa actttaaatc ttttagaaaa 600
taatatagaa gcatgccatc atgacttcag tgtagagaaa aatttcttat gactcaaagt 660
cctaaccaca aagaaaagat tgttaattag attgcatgaa tattaagact tatttttaaa 720
attaaaaaac cattaagaaa agtcaggcca tagaatgaca gaaaatattt gcaacacccc 780
agtaaagaga attgtaatat gcagattata aaaagaagtc ttacaaatca gtaaaaaata 840
tttctagaca aaaatttgaa cagatgaaag agaaactcta aataatcatt acacatgaga 900
aactcaatct cagaaatcag agaactatca ttgcatatac actaaattag agaaatatta 960
aaaggctaag taacatctgt ggcaatattg atggtatata accttgatat gatgtgatga 1020
gaacagtact ttaccccatg ggcttcctcc ccaaaccctt accccagtat aaatcatgac 1080
aaatatactt taaaaaccat taccctatat ctaaccagta ctcctcaaaa ctgtcaaggt 1140
catcaaaaat aagaaaagtc tgaggaactg tcaaaactaa gaggaaccca aggagacatg 1200

-continued

```
agaattatat gtaatgtggc attctgaatg agatcccaga acagaaaaag aacagtagct   1260

aaaaaactaa tgaaatataa atattttttg aactttagtt ttttttaaaa aagagtagca   1320

ttaacacggc aaagccattt tcatattttt cttgaacatt aagtacaagt ctataattaa   1380

aaatttttta aatgtagtct ggaacattgc cagaaacaga agtacagcag ctatctgtgc   1440

tgtcgcctaa ctatccatag ctgattggtc taaaatgaga tacatcaacg ctcctccatg   1500

tttttgtttt tctttttaaa tgaaaaactt tattttttaa gaggagtttc aggttcatag   1560

caaaattgag aggaaggtac attcaagctg aggaagtttt cctctattcc tagtttactg   1620

agagattgca tcatgaatgg gtgttaaatt ttgtcaaatg ctttttctgt gtctatcaat   1680

atgaccatgt gattttcttc tttaacctgt tgatgggaca aattacgtta attgattttc   1740

aaacgttgaa ccacccttac atatctggaa tattttctac ttggttgtgg tgtatatttt   1800

ttgatacatt cttggattct ttttgctaat attttgttga aaatgtttgt atctttgttc   1860

atgagagata ttggtctgtt gttttctttt cttgtaatgt cattttctag ttccggtatt   1920

aaggtaatgc tggcctagtt gaatgattta ggaagtattc cctctgcttc tgtcttctga   1980

aagagattgt agaaagttga tacaattttt ttttctttaa atatttgata gaattcttac   2040

tgacatccac tttgcctttc tctccacagg tgtccactcg gatcc                   2085
```

<210> SEQ ID NO 21
<211> LENGTH: 868
<212> TYPE: DNA
<213> ORGANISM: Artificial Sequence
<220> FEATURE:
<223> OTHER INFORMATION: Splice donor-human Interferon beta M18 S/MAR-splice acceptor flanked by 5' BglII site and 3' BamHI restriction enzyme sites

<400> SEQUENCE: 21

```
agatctatgc atgcagaagt tggtcgtgag gcactgggca ggtaagtatc aaggttacaa     60

gacaggtctc gagaagcttg atctaaataa acttataaat tgtgagagaa attaatgaat    120

gtctaagtta atgcagaaac ggagagacat actatattca tgaactaaaa gacttaatat    180

tgtgaaggta tactttcttt ccacataaat ttgtagtcaa tatgttcacc ccaaaaaagc    240

tgtttgttaa cttgccaacc tcattctaaa atgtatatag aagcccaaaa gacaataaca    300

aaaatattct tgtagaacaa aatgggaaag aatgttccac taaatatcaa gatttagagc    360

aaagcatgag atgtgtgggg atagacagtg aggctgataa aatagagtag agctcagaaa    420

cagacccatt gatatatgta agtgacctat gaaaaaaata tggcatttta caatgggaaa    480

atgatgatct ttttcttttt tagaaaaaca gggaaatata tttatatgta aaaaataaaa    540

gggaacccat atgtcatacc atacacacaa aaaaattcca gtgaattata agtctaaatg    600

gagaaggcaa aactttaaat cttttagaaa ataatataga agcatgccat catgacttca    660

gtgtagagaa aaatttctta tgactcaaag tcctaaccac aaagaaaaga ttgttaatta    720

tgaatgattt aggaagtatt ccctctgctt ctgtcttctg aaagagattg tagaaagttg    780

atacaatttt tttttcttta aatatttgat agagaattct tactgacatc cactttgcct    840

ttctctccac aggtgtccac tcggatcc                                       868
```

<210> SEQ ID NO 22
<211> LENGTH: 927
<212> TYPE: DNA
<213> ORGANISM: Artificial Sequence
<220> FEATURE:
<223> OTHER INFORMATION: Splice donor-805 bp human Apolipoprotein B -continued S/MAR-splice acceptor flanked by 5' BglII site and 3' BamHI
restriction enzyme sites

<400> SEQUENCE: 22
agatctatgc atgcagaagt tggtcgtgag gcactgggca ggtaagtatc aaggttacaa 60
gacaggtctc gaggcctacc ggagagcctt gccttgcaaa ggcagacagt cagtgaggaa 120
gactatgtgg cacatgaaga caccagaggt gttcctcagg atcaaagtat gtacaagcct 180
ttgtgaatat tttttccttc tcacttggca aatacaattc ctgagatcaa taacctcgtc 240
tttttaattt tttcctcgtc tttttaacta tttataaaat attgaattat aaaatatgta 300
attataaata ctttaattat aaaatatgta attataaata ctttaattat aaaatatgta 360
attataaata ctttataaaa tatgtaatta taaaatatgt aattataaac attttaatta 420
taaaatatgt aattataaac attttaatta taaaatatgt aattataaac attttaatta 480
taaaatatgt aattataaac attttaatta taaaatatgt aattataaac attttaatta 540
taaaatattt aattataaac attttaatta taaaatattt aattataaat attttaatta 600
taaaatattt aattataaat attttaatta taaaatattt aattataaat attttaatta 660
taaaatattt aattataaat actttaatta taaaatattt aattataaat attttaatta 720
taaaatattt aattataaat attttaatta taaatatttt aattataaaa tatttaatta 780
taaaaacaca attacctcat ctttttaaat atttttgcaa aatatttccc tccataattt 840
ctccgtttcc atttttattc tgttacttaa atgaattctt actgacatcc actttgcctt 900
tctctccaca ggtgtccact cggatcc 927

<210> SEQ ID NO 23
<211> LENGTH: 647
<212> TYPE: DNA
<213> ORGANISM: Artificial Sequence
<220> FEATURE:
<223> OTHER INFORMATION: Splice donor-525 bp human Apolipoprotein B
S/MAR-splice acceptor flanked by 5' NsiI site and 3' BamHI
restriction enzyme sites

<400> SEQUENCE: 23
atgcatgcag aagttggtcg tgaggcactg ggcaggtaag tatcaaggtt acaagacagg 60
tctcgagatt tataaaatat tgaattataa aatatgtaat tataaatact ttaattataa 120
aatatgtaat tataaatact ttaattataa aatatgtaat tataaatact ttataaaata 180
tgtaattata aaatatgtaa ttataaacat tttaattata aaatatgtaa ttataaacat 240
tttaattata aaatatgtaa ttataaacat tttaattata aaatatgtaa ttataaacat 300
tttaattata aaatatgtaa ttataaacat tttaattata aaatatttaa ttataaacat 360
tttaattata aaatatttaa ttataaatat tttaattata aaatatttaa ttataaatat 420
tttaattata aaatatttaa ttataaatat tttaattata aaatatttaa ttataaatac 480
tttaattata aaatatttaa ttataaatat tttaattata aaatatttaa ttataaatat 540
tttaattata aatattttaa ttataaaata tttaattata aaaacacaat tagaattctt 600
actgacatcc actttgcctt tctctccaca ggtgtccact cggatcc 647

<210> SEQ ID NO 24
<211> LENGTH: 197
<212> TYPE: DNA
<213> ORGANISM: Artificial Sequence
<220> FEATURE:
<223> OTHER INFORMATION: pCI intron

<400> SEQUENCE: 24
gcagaagttg gtcgtgaggc actgggcagg taagtatcaa ggttacaaga caggtttaag 60
gagaccaata gaaactgggc ttgtcgagac agagaagact cttgcgtttc tgataggcac 120
ctattggtct tactgacatc cactttgcct ttctctccac aggtgtccac tcccagttca 180
attacagctc ttaaggc 197

<210> SEQ ID NO 25
<211> LENGTH: 42
<212> TYPE: DNA
<213> ORGANISM: Artificial Sequence
<220> FEATURE:
<223> OTHER INFORMATION: pCI Splice donor

<400> SEQUENCE: 25
gcagaagttg gtcgtgaggc actgggcagg taagtatcaa gg 42

<210> SEQ ID NO 26
<211> LENGTH: 44
<212> TYPE: DNA
<213> ORGANISM: Artificial Sequence
<220> FEATURE:
<223> OTHER INFORMATION: pCI Splice acceptor (murine IgG)

<400> SEQUENCE: 26
cttactgaca tccactttgc ctttctctcc acaggtgtcc actc 44

<210> SEQ ID NO 27
<211> LENGTH: 1025
<212> TYPE: DNA
<213> ORGANISM: Artificial Sequence
<220> FEATURE:
<223> OTHER INFORMATION: Ele40 expression enhancer

<400> SEQUENCE: 27
gatcaagaaa gcactccggg ctccagaagg agccttccag gccagctttg agcataagct 60
gctgatgagc agtgagtgtc ttgagtagtg ttcagggcag catgttacca ttcatgcttg 120
acttctagcc agtgtgatga gaggctggag tcaggtctct agagagttga gcagctccag 180
ccttagatct cccagtctta tgcggtgtgc ccattcgctt tgtgtctgca gtcccctggc 240
cacacccagt aacagttctg ggatctatgg gagtagcttc cttagtgagc tttcccttca 300
aatactttgc aaccaggtag agaagtttgg agtgaaggtt ttgttctttg tttcttcaca 360
atatggatat gcatcttctt ttgaaaatgt taaagtaaat tacctctctt ttcagatact 420
gtcttcatgc gaacttggta tcctgtttcc atcccagcct tctataaccc agtaacatct 480
tttttgaaac cagtgggtga gaaagacacc tggtcaggaa cgcggaccac aggacaactc 540
aggctcaccc acggcatcag actaaaggca aacaaggact ctgtataaag taccggtggc 600
atgtgtatta gtggagatgc agcctgtgct ctgcagacag ggagtcacac agacactttt 660
ctataatttc ttaagtgctt tgaatgttca agtagaaagt ctaacattaa atttgattga 720
acaattgtat attcatggaa tattttggaa cggaatacca aaaaatggca atagtggttc 780
tttctggatg gaagacaaac ttttcttttt aaattttatc ttatatattt gaggttgacc 840
acatgacctt aaggatacat atagacagta aactggttac tacagtgaag caaattaaca 900
tatctaccat cttacatagt tacatttttt tgtgtgacag gaacagctaa aatctacgta 960
tttaacaaaa atcctaaaga caatacattt ttattaacta tagccctcat gatgtacatt 1020
agatc 1025

<210> SEQ ID NO 28
<211> LENGTH: 1503
<212> TYPE: DNA
<213> ORGANISM: Artificial Sequence
<220> FEATURE:
<223> OTHER INFORMATION: A2UCOE expression enhancer

<400> SEQUENCE: 28
gcctacagct caagccacat ccgaaggggg agggagccgg gagctgcgcg cggggccgcc 60
ggggggaggg gtggcaccgc ccacgccggg cggccacgaa gggcggggca gcgggcgcgc 120
gcgcggcggg gggaggggcc ggcgccgcgc ccgctgggaa ttggggccct agggggaggg 180
cggaggcgcc gacgaccgcg gcacttaccg ttcgcggcgt ggcgcccggt ggtccccaag 240
gggagggaag gggaggcgg ggcgaggaca gtgaccggag tctcctcagc ggtggctttt 300
ctgcttggca gcctcagcgg ctggcgccaa aaccggactc cgcccacttc ctcgcccgcc 360
ggtgcgaggg tgtggaatcc tccagacgct gggggagggg gagttgggag cttaaaaact 420
agtacccctt tgggaccact ttcagcagcg aactctcctg tacaccaggg gtcagttcca 480
cagacgcggg ccaggggtgg gtcattgcgg cgtgaacaat aatttgacta gaagttgatt 540
cgggtgtttc cggaaggggc cgagtcaatc cgccgagttg gggcacggaa aacaaaaagg 600
gaaggctact aagatttttc tggcgggggt tatcattggc gtaactgcag ggaccacctc 660
ccgggttgag gggctggat ctccaggctg cggattaagc ccctcccgtc ggcgttaatt 720
tcaaactgcg cgaccgtttc tcacctgcct tgcgccaagg caggggcgg gaccctattc 780 caagaggtag taactagcag gactctagcc ttccgcaatt cattgagcgc atttacggaa 840
gtaacgtcgg gtactgtctc tggccgcaag ggtgggagga gtacgcattt ggcgtaaggt 900
ggggcgtaga gccttcccgc cattggcggc ggatagggcg tttacgcgac ggcctgacgt 960
agcggaagac gcgttagtgg gggggaaggt tctagaaaag cggcggcagc ggctctagcg 1020
gcagtagcag cagcgccggg tcccgtgcgg aggtgctcct cgcagagttg tttctcgagc 1080
agcggcagtt ctcactacag cgccaggacg agtccggttc gtgttcgtcc gcggagatct 1140
ctctcatctc gctcggctgc gggaaatcgg gctgaagcga ctgagtccgc gatggaggta 1200
acgggtttga aatcaatgag ttattgaaaa gggcatggcg aggccgttgg cgcctcagtg 1260
gaagtcggcc agccgcctcc gtgggagaga ggcaggaaat cggaccaatt cagtagcagt 1320
ggggcttaag gtttatgaac ggggtcttga gcggaggcct gagcgtacaa acagcttccc 1380
caccctcagc ctcccggcgc catttccctt cactgggggt gggggatggg gagctttcac 1440
atggcggacg ctgccccgct ggggtgaaag tggggcgcgg aggcgggaat tcttattccc 1500
ttt 1503

<210> SEQ ID NO 29
<211> LENGTH: 15
<212> TYPE: DNA
<213> ORGANISM: Artificial Sequence
<220> FEATURE:
<223> OTHER INFORMATION: Splice acceptor consensus sequence

<400> SEQUENCE: 29
yyyyyyyyyy yagrw 15